(12) United States Patent
Drzewuki et al.

(10) Patent No.: US 9,965,817 B1
(45) Date of Patent: May 8, 2018

(54) METHODS AND SYSTEMS FOR REBATE MODELING

(75) Inventors: Danielle L. Drzewuki, Arnold, MO (US); Todd N. Teixeira, North Kingstown, RI (US); Ben A. Unk, Fenton, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 230 days.

(21) Appl. No.: 13/619,809

(22) Filed: Sep. 14, 2012

Related U.S. Application Data

(60) Provisional application No. 61/534,662, filed on Sep. 14, 2011.

(51) Int. Cl.
*G06Q 30/02* (2012.01)
*G06Q 10/06* (2012.01)
*G06Q 20/00* (2012.01)
*G06Q 50/22* (2018.01)

(52) U.S. Cl.
CPC ......... *G06Q 50/22* (2013.01); *G06Q 30/0234* (2013.01)

(58) Field of Classification Search
CPC .... G06Q 10/10; G06Q 10/1057; G06Q 50/24; G06F 19/323; G06F 19/326; G06F 19/328; G06F 19/3456
USPC .............................................................. 705/2
See application file for complete search history.

(56) References Cited

U.S. PATENT DOCUMENTS

| 8,112,287 | B1 | 2/2012 | Paul et al. | |
|---|---|---|---|---|
| 8,112,288 | B1 | 2/2012 | Paul et al. | |
| 8,239,213 | B1 | 8/2012 | Paul et al. | |
| 8,494,877 | B1 | 7/2013 | Paul et al. | |
| 8,521,551 | B1 * | 8/2013 | Paul et al. | 705/2 |
| 2001/0037216 | A1 * | 11/2001 | Oscar et al. | 705/2 |
| 2002/0169727 | A1 * | 11/2002 | Melnick et al. | 705/400 |
| 2004/0073457 | A1 * | 4/2004 | Kalies | 705/2 |

* cited by examiner

*Primary Examiner* — Hiep V Nguyen
(74) *Attorney, Agent, or Firm* — Bryan Cave Leighton Paisner LLP

(57) ABSTRACT

Methods and systems for rebate modeling are described. In an embodiment, a formulary of a plan sponsor is accessed. Prescription drug utilization data is accessed. Drug pricing information is accessed. Benefit design including co-pay structure of the plan sponsor is accessed. A plan sponsor rebate for a drug classification is calculated. An alternate plan sponsor rebate is calculated based on a formulary modification, a benefit design modification, or both the formulary modification and the benefit design modification. A difference between the plan sponsor rebate and alternate plan sponsor rebate is determined. A display is generated based on a determination of the difference. Additional methods and systems are disclosed.

22 Claims, 35 Drawing Sheets

METHODS AND SYSTEMS FOR REBATE MODELING

RELATED APPLICATIONS

This application claims the benefit of U.S. Provisional Patent Application No. 61/534,662 filed on 14 Sep. 2011, the entire contents of which are herein incorporated by reference.

FIELD

The field relates to drug rebates, and more particularly to a method and system for modeling prescription drug rebates.

BRIEF DESCRIPTION OF THE DRAWINGS

FIGS. 8-36 illustrate example displays, according to example embodiments; and

DETAILED DESCRIPTION

Figure 1:
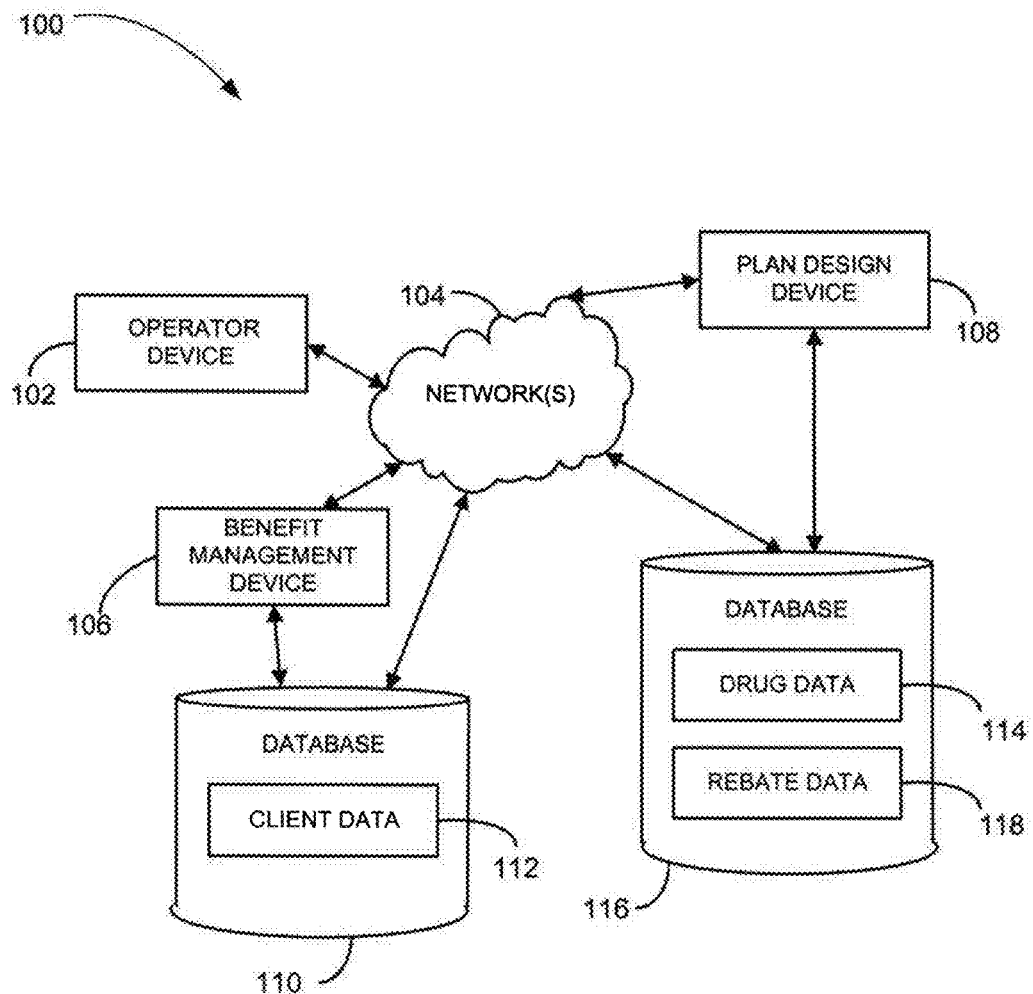
FIG. 1 is a block diagram of an example system, according to an example embodiment.

Methods and systems for rebate modeling are described. Methods and systems for rebate modeling may be used in connection with benefit plan design or may otherwise be used. Modeling refers broadly to providing options for plan design, facilitating selections among those options, and illustrating the effect of the selected options on rebates and other aspects of plan design. In the following description, for purposes of explanation, numerous specific details are set forth in order to provide a thorough understanding of example embodiments. It will be evident, however, to one of ordinary skill in the art these embodiments may be practiced without these specific details.

A client or benefit plan sponsor, such as an employer, health insurer, or other entity and/or cooperative group may provide a drug or pharmaceutical benefit plan for a set of members. The members may include a participant or cardholder in a pharmaceutical benefit plan (e.g., an employee of the client) or a beneficiary of the participant (e.g., a spouse or a child of the beneficiary). In selecting and/or designing a pharmaceutical benefit plan, a plan sponsor may consider the costs associated with various aspects of a plan design. Financial considerations and/or implications of a pharmaceutical benefit plan design may include and/or be based upon one or more of: rebate guarantees, prescription drug programs, benefit design choices, formulary design, rebate contracts, and patent expirations.

Formulary design may include identification of drugs within drug classes and selection and/or other plan design differentiation among those drugs. Drugs may be categorized by drug class. A drug class may be defined according to a condition a drug is used to treat and/or the mode of therapeutic action. The drug class of a drug may be defined differently depending upon the desired level of specificity and/or the intended purpose of the drug class designation. For example, the drug class of a drug may be "anticonvulsant" or it may be "calcium channel modifying agent," depending upon the desired degree of specificity. Other examples of drug class include heart and circulatory drugs and the more specific angiotensin converting enzyme inhibitors; gastrointestinal agents and the more specific proton pump inhibitors; and immunological agents, the more specific immune stimulants, and the even more specific vaccines to prevent diphtheria.

Identifications of drug class and determinations of which drugs are in a particular drug class may be made by pharmacists, other healthcare professionals, or may be otherwise made. A person identifying a drug class and/or determining whether a particular drug falls within that class may have some discretion in making such decisions. A drug class may include brand drugs, generic drugs, or both.

Drug manufacturers may offer rebates for their products. A rebate may provide an end result that is similar to a price reduction, but may be more effective than a price reduction in promoting decisions such as formulary position and/or benefit co-pay design. Thus, rebates may vary based on a product's formulary position and/or benefit co-pay design. In an example, a formulary position may be described as limited, preferred, or exclusive in which a limited formulary position is one in which the particular drug is one of several in a drug class; a preferred formulary position is one in which the particular drug is one of two in a drug class; and an exclusive formulary position is one in which the particular drug is the only drug in a drug class. In determining whether a formulary position is limited, preferred, or exclusive, consideration is given only to brand drugs within the drug class.

Benefit co-pay design generally refers to classification of the co-pay component of a pharmaceutical benefit plan. By way of example, a moderate benefit co-pay design refers to one in which there is little or no differentiation between formulary and non-formulary drugs, a high benefit co-pay design refers to one in which the co-pay differential between formulary and non-formulary drugs reaches a designated threshold (e.g., $5, $10, or other threshold amount), and closed benefit co-pay design refers to one in which a member must pay 100% of the cost of a non-formulary drug.

By way of example, a grid-like system may be applied to establish a rebate, e.g., as follows:

| Limited formulary position/moderate benefit copay design | Limited formulary position/high benefit co-pay design | Limited formulary position/closed benefit co-pay design |
| --- | --- | --- |
| Preferred formulary position/moderate benefit copay design | Preferred formulary position/high benefit co-pay design | Preferred formulary position/closed benefit co-pay design |

| Exclusive formulary position/moderate benefit copay design | Exclusive formulary position/high benefit co-pay design | Exclusive formulary position/closed benefit co-pay design |
| --- | --- | --- |

In the formulary position/benefit design scenario depicted in the bottom right corner of the grid (referred to as a closed exclusive position), a manufacturer of the drug on formulary may be willing to offer a much more significant rebate than a manufacturer whose drug is in a formulary position/benefit co-pay design scenario such as the one depicted in the middle. A manufacturer whose drug is in a formulary position/benefit co-pay design scenario such as the one depicted in the top left corner may be unwilling to offer any rebate.

Other factors may affect the rebate offered by a drug manufacturer. For example, a drug manufacturer's rebate may differ based on the particular plan sponsor to whom it is being offered, whether a step therapy program is imposed in connection with a drug manufacturer's drug, and other factors that may be relevant to a drug manufacturer. Step therapy generally refers to a method of care in which, for example, a patient with a particular condition must try a generic drug in the appropriate drug class to treat the condition and only then may be provided a benefit for use of a brand drug within the appropriate drug class when treatment with the generic drug is unsuccessful. In other types of step therapy, the patient must try a lesser cost drug in the appropriate drug class and only then may be provided a benefit for use of a more expensive drug within the appropriate drug class when treatment with the lesser cost drug is unsuccessful.

A brand drug manufacturer may stop offering a rebate and/or may change a rebate program upon expiration of patent protection for the particular brand drug or upon generic launch. Identification of a drug as a brand drug generally refers to the drug as an innovator drug; specifically, a drug originally marketed under an original new drug application (NDA) approved by the Food and Drug Administration (FDA). The term generic drug generally refers to a drug for which there is no current patent protection in the relevant jurisdiction.

A drug manufacturer may offer a rebate directly to a plan sponsor and/or may offer a drug rebate to a pharmaceutical benefit manager (PBM) that administers a prescription drug benefit plan for one or more plan sponsors. A PBM may, in some instances, then offer all or a portion of a manufacturer's rebate to the plan sponsor. A PBM's sharing of a manufacturer's rebate may take the form of a rebate guarantee. Thus, a plan sponsor may pay an amount for members' use of a particular drug throughout the year, then based on contracted terms, the PBM would issue a payment based on the rebate guarantee. A PBM may receive a payment from a drug manufacturer based, for example, on use of the drug by members of the PBM's plan sponsor or plan sponsors.

In some embodiments, a PBM and its plan sponsor agree in advance to a rebate guarantee which will be paid (or otherwise credited) by the PBM to the plan sponsor regardless of the actual use of the drug to which the rebate applies or the actual rebate, if any, received by the PBM from the drug manufacturer. In other embodiments, the rebate guarantee provided by a PBM to its plan sponsor may be correlated to actual drug use by the client's members and/or the actual rebate received by the PBM from the drug manufacturer.

Systems and methods described and disclosed herein may be used in pharmaceutical benefit plan design and may include functionality to calculate rebates and/or guaranteed rebates based on alternative scenarios that depict, for example, differences in drugs' formulary positions and/or in a benefit co-pay design. Other financial modeling functionality may be included in the systems and methods or pharmaceutical benefit plan design.

In some embodiments, the methods and systems may be used by pharmacists or other professionals at a PBM or by another user: to provide guidance to plan sponsors who are determining formulary position for a given drug class; to determine or estimate the net cost associated with a particular drug to a plan sponsor; to determine or estimate the financial impacts of implementing a step therapy program; to calculate a prorated plan sponsor guarantee over a period of time, such as a 3-5 year span; to determine the financial impact of year over year changes to rebate contracts; to promote leveraging a PBM's rebate contracts to determine an optimal rebate guarantee for prospective plan sponsors; and/or determine or estimate the overall financial impact of annual formulary changes, patent expirations, inflation, and rebate contract changes year over year for book of business projections.

In some embodiments, the components that may be utilized in the rebate calculation(s) may include one or more of the following:

(A) Calculate base cost (e.g., based on current WAC pricing and client specific contract pricing detail)
(B) Calculate formulary position (e.g., original or modified)
(C) Apply select client option, if applicable, to use client specific rate
(D) Apply weights for benefit design (e.g., Open, Tiered, Closed)
(E) Step therapy modifiers (e.g., modified weighting)
(F) Apply enhancements that modify formulary position/ benefit design weights
(G) Find rates based on previous steps
(H) Calculate weighted rate
(I) Mail/retail weighted cost
(J) Copay accounted for in net cost
(K) Patent loss, annual contract improvement, and inflation accounted for, on a pro-rated basis.

FIG. 1 is a block diagram of an example system 100, according to an example embodiment. The system 100 includes an operator device 102 that facilitates access to tools and features of the system 100 by a user. The user may be, by way of example, a plan designer or other employee or agent of a PBM, a plan sponsor, or a different user. The user may use the operator device 102 to gather data points for client data 112, drug data 114, and/or rebate data 118 stored in a database 110, 116. In some embodiments, modification to the rebate models may not update the client data 112, the drug data 114, and/or the rebate data 118. The operator device 102 generates output to illustrate, among other things, the projected financial impact of formulary decisions and/or benefit co-pay design options.

A benefit management device 106 may be in communication with the operator device 102 over a network 104. The benefit management device 106 is a device generally operated by or on behalf of a benefit manager. For example, the benefit management device 106 may include claims adjudication functionality.

Some of the operations of the PBM that operates the benefit management device 106 may include the following. A member of a pharmacy benefit plan administered by or through the PBM (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location. The member may also obtain a prescription drug directly or indirectly through the use of a machine, such as a kiosk, vending unit, mobile electronic device, or a different type of computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary of the member to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process. Adjudication may be performed through the use of a machine, such as a computer system.

The amount of reimbursement paid to the pharmacy by a plan sponsor and/or member may be based at least in part on the type of pharmacy network in which the pharmacy is included. Other factors may be used to determine the reimbursement amount in addition to the type of pharmacy network.

A plan design device 108 may be operated by an entity associated with plan design and be in communication over a network 104. An operator of the plan design device 108 may use it to project the financial impact of formulary decisions.

In some embodiments, the operator device 102, the benefit management device 106, and the plan design device 108 are operated by a single entity. In other embodiments, the operator device 102, the benefit management device 106, and the plan design device 108 are operated by different entities. In some embodiments, the operator device 102, the benefit management device 106, and/or the plan design device 108 are combined into a single device, while in other embodiments, the operator device 102, the benefit management device 106, and the plan design device 108 operate on separate devices. For example, the functionality of the design plan device 108 may be included in the benefit manager device 106.

Examples of the devices 102, 106, 108 include a gaming unit, a mobile phone, a personal digital assistant (PDA), a display device, a generic or specialized computing system, or the like. Other devices may also be used. The devices 102, 106, 108 may each be the same type of device, or may be different types of devices.

While the system 100 in FIG. 1 is shown to include single devices 102, 106, 108, multiple devices may be used. Furthermore, while the system 100 in FIG. 1 is shown to include databases 110, 116, a single database may be used and/or additional databases may be provided. For example, the client data 112 may be stored in the database 116.

A user may be an operator device operator, a benefit management device operator, a plan design device operator, and/or may operate one or more other devices.

Examples of the network 104 by which devices 102, 104, 106, and databases 110, 116 may communicate include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may also include optical communications. Other conventional and/or later developed wired and wireless networks may also be used.

In some embodiments, the system 100 may include dynamically modeling a client's rebate and/or rebate guarantee based on benefit co-pay design, formulary design, anticipated rebate contract changes, patent expiration, client-specific rebate programs, and/or other aspects of a pharmaceutical benefit plan.

Figure 2:
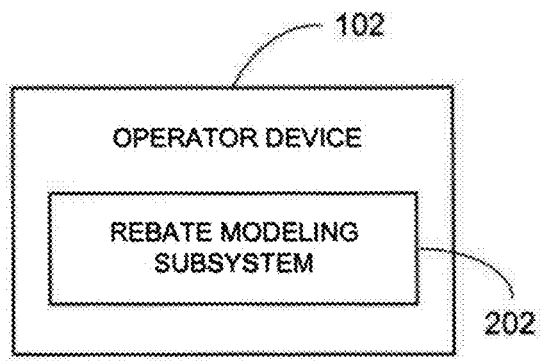
FIG. 2 is a block diagram of an example operator device that may be deployed within the system of FIG. 1, according to an example embodiment.

FIG. 2 illustrates the operator device 102, according to an example embodiment. The operator device 102 may be used by the device operator to model rebates and/or rebate guarantees. The operator device 102 may be deployed in the system 100, or may otherwise be used.

Figure 3:
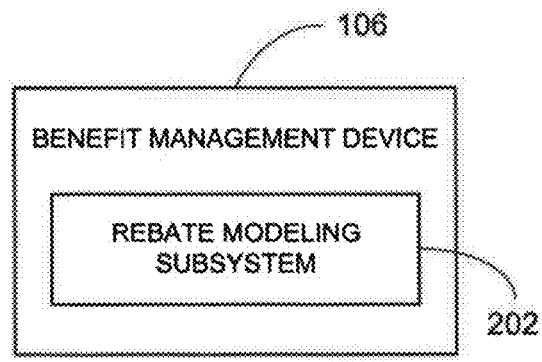
FIG. 3 is a block diagram of an example benefit management device that may be deployed within the system of FIG. 1, according to an example embodiment.

FIG. 3 illustrates the benefit management device 106, according to an example embodiment. The benefit management device 106 may be used by a benefit manager to model rebates and/or rebate guarantees. The benefit management device 106 may be deployed in the system 100, or may otherwise be used.

Figure 4:
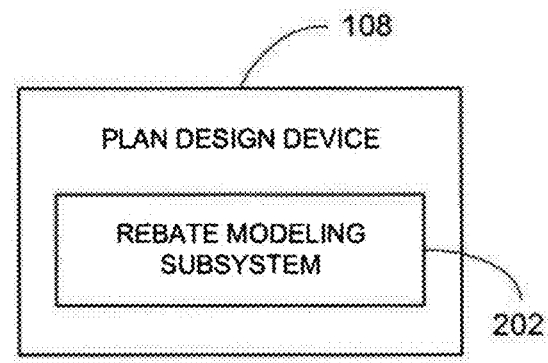
FIG. 4 is a block diagram of an example plan design device that may be deployed within the system of FIG. 1, according to an example embodiment.

FIG. 4 illustrates the plan design device 108, according to an example embodiment. The plan design device 108 may be used by a plan design to model rebates and/or rebate guarantees. The plan design device 108 may be deployed in the system 100, or may otherwise be used.

Figure 5:
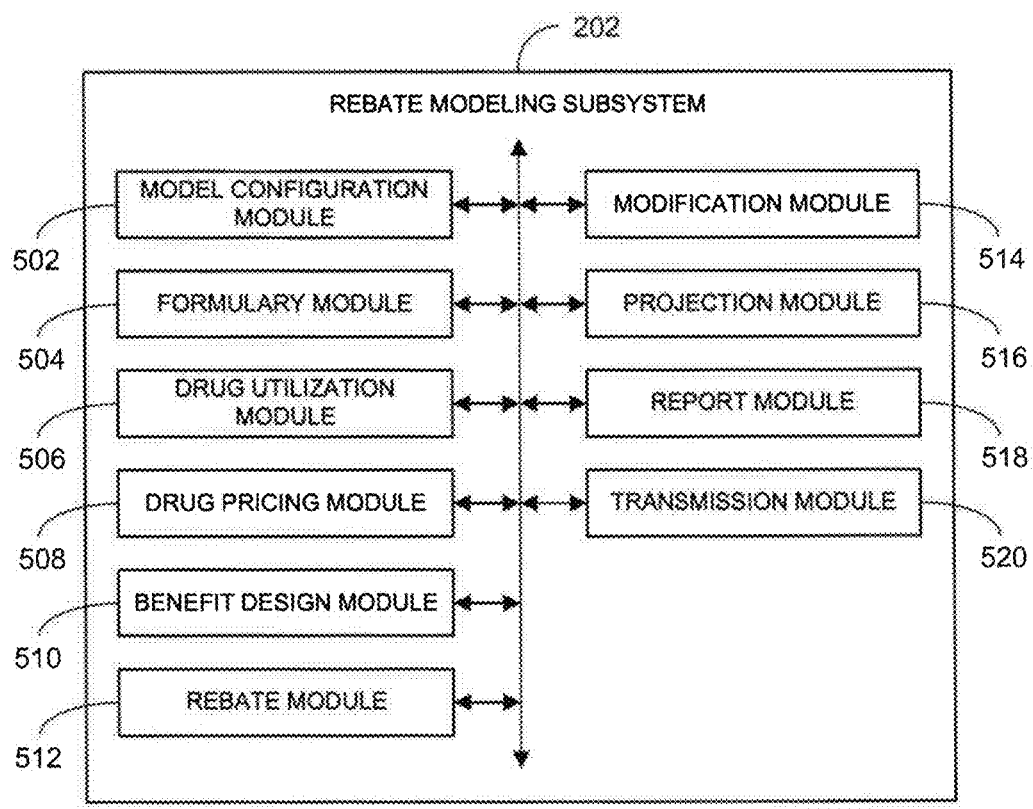
FIG. 5 is a block diagram of an example rebate modeling subsystem that may be deployed within the operator device of FIG. 2, the benefit management device of FIG. 3, or the plan design device 108 according to an example embodiment.

FIG. 5 illustrates an example rebate modeling subsystem 202 that may be deployed in the operator device 102, the benefit management device 106, the plan design device 108, or otherwise deployed in another system. One or more modules are communicatively coupled and included in the rebate modeling subsystem 202 to enable rebate modeling (e.g., for rebates and/or rebate guarantees. The modules of the rebate modeling subsystem 202 that may be included are a module configuration module 502, a formulary module 504, a drug utilization module 506, a drug pricing module 508, a benefit design module 510, a rebate module 512, a modification module 514, a projection module 516, a report module 518, and a transmission module 520. Other modules may also be included.

In some embodiments, the modules of the modeling subsystem 202 may be distributed so that some of the modules are deployed in the operator device 102 and some modules are deployed in the benefit management device 106 and/or the plan design device 108. In one embodiment, the modules are deployed in memory and executed by a processor coupled to the memory. The functionality contained within the modules 502-520 may be combined into a lesser number of modules, further divided among a greater number of modules, or redistributed among existing modules. Other configurations including the functionality of the modules 502-520 may be used.

The model configuration module 502 may be used to configure the modeling subsystem 202 for modeling rebates and/or rebate guarantees. In some embodiments, the configuration may include plan sponsor specific model options, scenario model options, co-pay options associated with the drug therapy class and, or rate parameter options. The elements of the configuration may be received (e.g., through operator selection), accessed from pre-stored options, or otherwise accessed.

In some embodiments, the rate parameter options include rate enhancements, rate exclusions, or both rate enhancements and rate exclusions.

In some embodiments, the plan sponsor specific model option includes an average wholesale price (AWP) discount for retail drug fills, mail order drug fills, or both retail drug and mail order drug fills, a business unit of a benefit manager, and/or a geographic region.

In some embodiments, the scenario model option includes a rebate year, a program type designation, prior authorizations designation, a home delivery designation, an include co-pay in net cost calculations designation, and/or a plan sponsor contract arrangements designation. In some embodiments, the scenario model option is applicable only to a specific scenario.

In some embodiments, the co-pay option associated with the drug therapy class is designated on a prescription drug basis or a percentage of average wholesale price for at least brand drugs and non-preferred brand drugs.

In some embodiments, the model configuration module 502 updates a baseline model used to calculate rebates and/or rebate guarantees.

The formulary module 504 uses and/or processes information regarding formularies in the rebate modeling subsystem 202. In some embodiments, the formulary module 502 accesses a formulary of a plan sponsor. The plan sponsor may have a single formulary or multiple formularies. In some embodiments, the formulary includes a custom formulary associated with plan sponsor separate from the benefit manager. In some embodiments, the formulary is associated with the benefit manager and used by the plan sponsor.

The drug utilization module 506 uses and/or processes information regarding prescription drug utilization. In some embodiments, the drug utilization module 506 accesses prescription drug utilization data. The prescription drug utilization data may be a portion of the client data 112 (see FIG. 1). The prescription drug utilization may be accessed for a certain time period of time. For example, the prescription drug utilization for a three-month period or a six-month period may be accessed. The periods may correspond to drug utilization during a single quarter or multiple quarters of a calendar year (e.g., the previous two quarters). The accessed prescription drug utilization data may be associated with a particular client, a particular grouping of clients, or a particular book of business.

The prescription utilization data as accessed by the drug utilization module 506 includes historic prescription drug information for patients of the plan sponsor. The historic prescription drug information may be for all patients of the plan sponsor, or a subset of all patients of the plan sponsor. In some embodiments, the historic prescription drug information may be for patients of multiple sponsors (e.g., across a book of business).

In general, the historic prescription drug information includes information regarding prescription drug usage of patients. Such historic prescription drug information may include a drug name of a prescription drug, a prescription drug unit of the prescription drug, a number of days supply of the prescription drug, and/or a fill location type (e.g., a retail pharmacy fill or a mail order pharmacy fill). Other information may also be a part of the historic prescription drug information.

In some embodiments, the prescription drug utilization data is at the National Drug Code 11 (NDC11) and mail/retail level. The mail/retail may be reflected by indicia to indicate the channel (e.g., retail delivery of a prescription drug or mail order delivery of the prescription drug) at which the prescription drugs were filled. The NDC11 refers to an industry standard, unique identifier for a prescription drug that identifies the drug, strength and manufacturer of the prescription drug.

In some embodiments, the historic prescription drug information includes indicia of a benefit tier at which the prescription drug was filled.

In some embodiments, the drug utilization module 506 includes processing patient drug utilization data to identify prescription drug utilization data and accessing prescription drug utilization data among the patient drug utilization data based on identification of the prescription drug utilization data.

In some embodiments, the model configuration module 502 receives a selection of a drug therapy class and a selection of a fill location type. The drug utilization module 506 may then access the prescription utilization data by the model configuration module 502 based on the receipt of the selection of the drug therapy class and the fill location type. In such embodiments, the drug utilization data accessed may include only a portion of available prescription utilization data that matches the drug therapy class and the fill location type.

The drug pricing module 508 uses and/or processes information regarding drug pricing information. In some embodiments, the drug pricing module 508 accesses drug pricing information. In some embodiments, the drug pricing information may be provided by Wolters Kluwer Health through its MEDI-SPAN product.

The benefit design module 510 uses and/or processes information regarding the benefit design of the plan sponsor. In general, the benefit design includes co-pay structure of the plan sponsor. In some embodiments, the benefit design module 510 accesses benefit design including co-pay structure of the plan sponsor.

The operations performed by modules 502-510 may occur sequentially in one or of a variety of different orders, may occur simultaneously, or may otherwise occur.

The rebate module 512 calculates prescription drug rebates. In general, the rebate module 512 calculates the rebate for a drug classification based on a formulary. The prescription drug rebate for a single drug classification may be calculated, or the prescription drug rebate may be calculated for multiple drug classifications. In some embodiments, the drug rebate calculated for multiple drug classifications is broken out by each drug classification. In some embodiments, the drug rebate calculated for multiple drug classifications is grouped together into a single dollar amount. In some embodiments, the drug classification is defined according to a condition that a prescription drug is used to treat. In some embodiments, the rebate may be used to determine, calculate, or recalculate a rebate guarantee.

In some embodiments, the prescription drug rebate is calculated for a past period of time. In some embodiments, the prescription drug rebate is calculated for a current period of time. In some embodiments, the prescription drug rebate is calculated for a future period of time.

In some embodiments, the rebate module 512 calculates a prescription drug rebate based on the prescription drug utilization associated with the drug classification, the drug pricing information associated with prescription drugs included in the drug classification, and the co-pay structure.

The rebate module 512 may calculate multiple prescription rebates according to certain modifications made to a base set of data. For example, a modification may cause prescription rebate to calculate a prescription drug rebate based on a modification to one or more of the prescription drug utilization associated with the drug classification, the drug pricing information associated with prescription drugs included in the drug classification, and the co-pay structure.

The modification module 514 may receive a modification and the rebate module 512 may calculate (or recalculate) a prescription rebate based on the modification. Examples of modifications that may be received by the modification module include a formulary modification and a benefit design modification. A single modification or multiple modifications may be received by the modification module 514 and may be part of a rebate calculation.

In some embodiments, the formulary modification includes adding an additional prescription drug within a drug classification to the formulary. Adding the additional prescription drug may enable patients of the plan sponsor to receive a drug benefit for the additional prescription drug. The co-pay required to be paid by the patient for the additional prescription drug may be defined by the co-pay setup of the plan design. The addition of the additional prescription drug may cause the rebate calculated by the rebate module 510 to be different.

In some embodiments, the formulary modification includes removing an existing prescription drug within the drug classification from the formulary. The removal of the prescription drug may limit patients of the plan sponsor from being able to receive a drug benefit for the removed prescription drug. The removal of the additional prescription drug may cause the rebate calculated by the rebate module 512 to be different.

In some embodiments, the benefit design modification includes applying a step therapy to the drug classification. The application of the step therapy may necessitate that a patient try one or more prescription drugs within the drug classification before being able to receive coverage (or coverage at a higher level) for one or more other prescription drugs. When a step therapy is applied to the drug classification, the rebate module 512 may automatically apply enhancements and enhanced rates, alter the formulary, and/or adjusting rebates associated with one or more drugs included the drug classification before calculating an alternate prescription rebate.

In some embodiments, the benefit design modification includes a market share modification applied to the drug classification. The calculation of the alternate plan sponsor rebate by the rebate module 512 may then include automatically applying exclusions based on a plan sponsor contract.

In some embodiments, the model configuration module 502 may access sponsor rebate data associated with the plan sponsor. The sponsor rebate data may include indicia of a rebate enhancement provided by a manufacturer of the drug to the plan sponsor. The calculation of the rebate guarantee by the rebate module 512 may then based on the formulary position of the drug and the rebate enhancement and the calculation of the additional rebate guarantee may be based on the modification to the formulary position of the drug and the rebate enhancement.

In some embodiments, the module configuration module 502 accesses benefit manager rebate data associated with a benefit manager. The benefit manager data may include an indicia of a rebate enhancement provided by a manufacturer of the drug to the benefit manager of a drug benefit offered through the plan sponsor. The calculation of the rebate guarantee by the rebate module 512 may then based on the formulary position of the drug and the rebate enhancement and the calculation of the additional rebate guarantee may be based on the modification to the formulary position of the drug and the rebate enhancement.

The projection module 516 may determine various projections based on prescription rebates calculated by the rebate module 512.

In some embodiments, the projection module 516 determines a difference between a plan sponsor rebate and an alternate plan sponsor rebate. The display module 518 may then generate a display based on a determination of the difference.

In some embodiments, the rebate module 512 calculates a product net of rebate based on the rebate guarantee and the alternate rebate guarantee. The projection determined by the projection module 516 may then based on the determination of the difference and the product net of rebate. In some embodiments, the projection determined by the projection module 516 identifies a lowest cost product based on calculation of the product net of rebate.

An example implementation of the rebate modeling system 502 includes the formulary module 504 to access a formulary of a plan sponsor and the drug utilization module to accessing prescription drug utilization data including historic prescription drug information of patients of the plan sponsor. The drug pricing module 508 may be deployed to access drug pricing information and the benefit design module 510 to access benefit design including co-pay structure of the plan sponsor.

In some embodiments, the projection module 516 accesses projected drug inflation information, rebate enhancements, and patent expiration information. The projection module 516 may then project future rebate information of the plan sponsor based on the formulary, the prescription drug utilization associated with the drug classification, the drug pricing information associated with a plurality of drugs including the drug classification, the co-pay structure, the projected drug inflation information, the rebate enhancements, and the patent expiration information.

In some embodiments, projecting the future rebate information by the projection module 516 includes automatically removing a prescription drug from the formulary beyond a certain period of time based on the patent expiration information. In some embodiments, projecting the future rebate information by the projection module 516 includes altering rebates of additional prescription drugs based on removal of the prescription drug from the formulary The report module 518, in some embodiments, generates a report based on projection of the future rebate information by the projection module 516.

When deployed, the transmission module 520 transmits future report information. For example, the future rebate information of the plan sponsor may be transmitted by the transmission module 520 to an underwriting device (not shown). The underwriting device may be a device operated by the benefit manager (or incorporated into the benefit management device(s) 106) and usable to determine an affect on a client guarantee based on the future rebate information.

Figure 6:
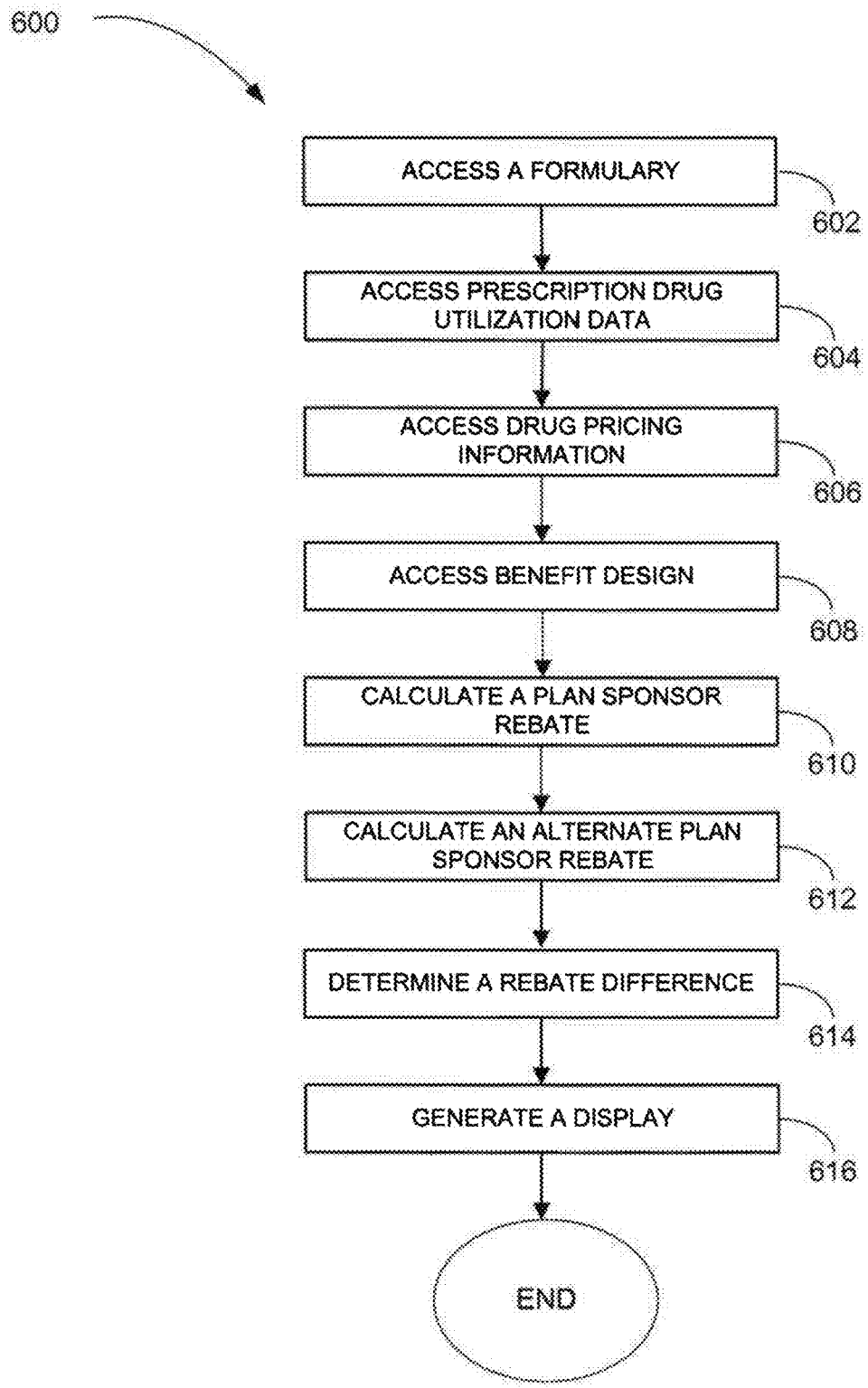
FIG. 6 is an example process flow illustrating a method for displaying rebate information, according to an example embodiment

FIG. 6 illustrates a method 600 for displaying rebate information, according to an example embodiment. The method 600 may be performed by the operator device 102, partially by the operator device 102 and partially by the benefit management device 106 and/or the plan design device 108, or may be otherwise performed.

A formulary of a plan sponsor is accessed at block 602. Prescription drug utilization data is accessed at block 604.

In some embodiments, a selection of a drug therapy class and a selection of a fill location type may be received. The accessing of the prescription utilization data may then be based on the receipt of the selection of the drug therapy class and the fill location type.

In some embodiments, the accessing of the prescription drug utilization includes processing patient drug utilization data to identify prescription drug utilization data and accessing prescription drug utilization data among the patient drug utilization data based on identification of the prescription drug utilization data.

The drug pricing information is accessed at block 606. The benefit design including co-pay structure of the plan sponsor is accessed at block 608.

A plan sponsor rebate for a drug classification is calculated at block 610 based on the formulary, the prescription drug utilization associated with the drug classification, the drug pricing information associated with a plurality of drugs including the drug classification, and the co-pay structure.

An alternate plan sponsor rebate is calculated at block 612 based on a formulary modification, a benefit design modification, or both the formulary modification and the benefit design modification.

In some embodiments, sponsor rebate data associated with the plan sponsor is accessed. The rebate client data may include indicia of a rebate enhancement provided by a manufacturer of the drug to the plan sponsor. Calculation of the rebate guarantee may then be based on the formulary position of the drug and the rebate enhancement and calculation of the additional rebate guarantee is based on the modification to the formulary position of the drug and the rebate enhancement.

In some embodiments, benefit manager rebate data associated with a benefit manager is accessed. The benefit manager data may include an indicia of a rebate enhancement provided by a manufacturer of the drug to the benefit manager of a drug benefit offered through the plan sponsor. The calculation of the rebate guarantee may then be based on the formulary position of the drug and the rebate enhancement. The calculation of the additional rebate guarantee may then based on the modification to the formulary position of the drug and the rebate enhancement.

A difference is determined between the plan sponsor rebate and alternate plan sponsor rebate at block 614.

A display is generated at block 616 based on a determination of the difference. In some embodiments, the display includes a projected dollar rebate per drug class. In some embodiments, the display includes an affect on a rebate guarantee.

In some embodiments, a product net of rebate may be calculated based on the rebate guarantee and the alternate rebate guarantee. Generation of the display may be based on the determination of the difference and the product net of rebate. In some embodiments, the display identifies a lowest cost product based on calculation of the product net of rebate.

Figure 7:
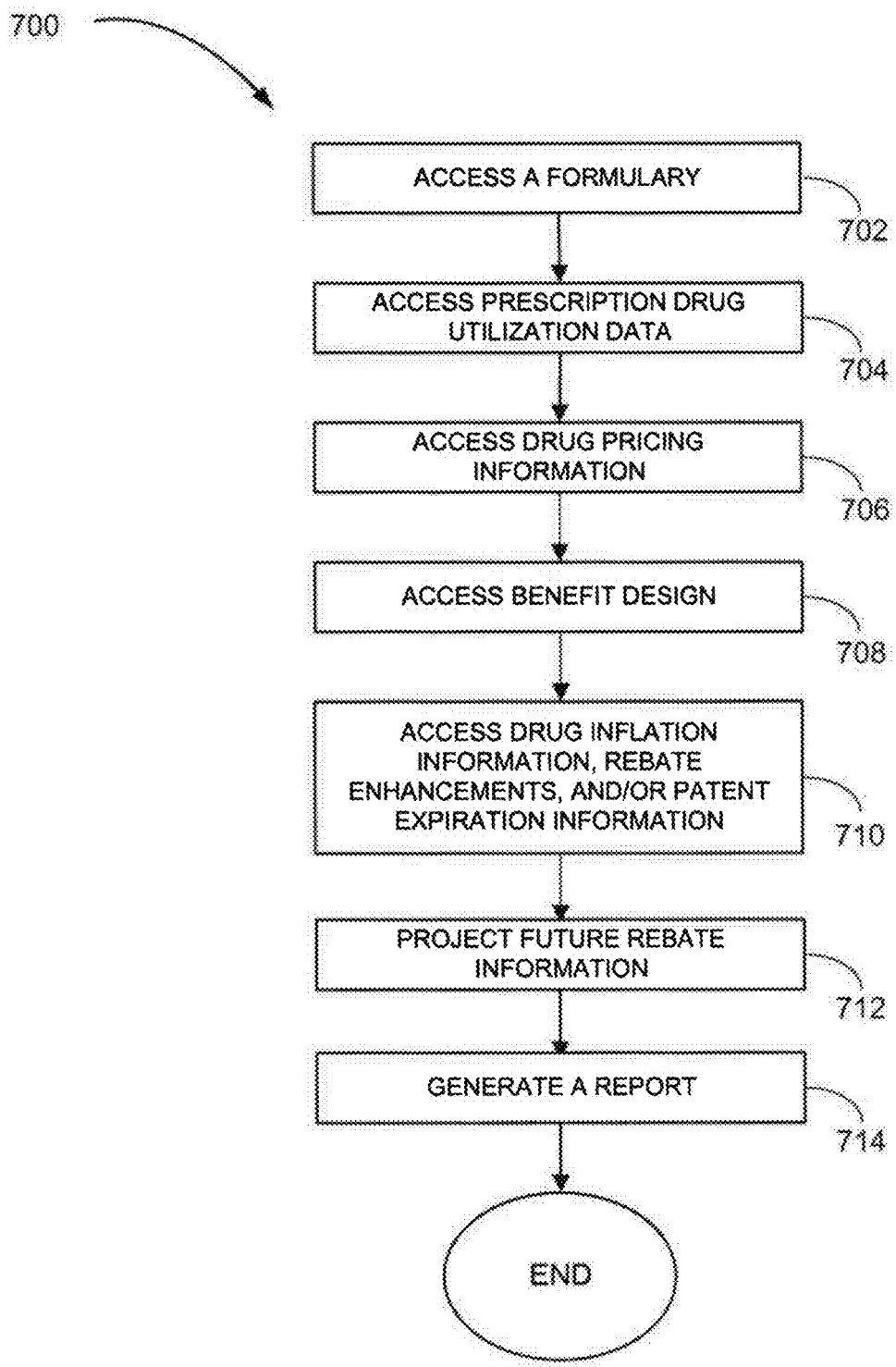
FIG. 7 is an example process flow illustrating a method for projecting future rebate information, according to an example embodiment.

FIG. 7 illustrates a method 700 for projecting future rebate information, according to an example embodiment. The method 700 may be performed by the operator device 102, partially by the operator device 102 and partially by the benefit management device 106 and/or the plan design device 108, or may be otherwise performed.

A formulary of a plan sponsor is accessed at block 702. Prescription drug utilization data is accessed at block 704. Drug pricing information is accessed at block 706. Benefit design including co-pay structure of the plan sponsor is accessed at block 708.

Projected drug inflation information, rebate enhancements, and/or patent expiration information are accessed at block 710.

At block 712, future rebate information of the plan sponsor is projected based on the formulary, the prescription drug utilization associated with the drug classification, the drug pricing information associated with drugs including the drug classification, the co-pay structure; the projected drug inflation information, the rebate enhancements, and/or the patent expiration information.

A report may be generated at block 714 based on projection of the future rebate information.

FIGS. 8 through 33 are example displays that may be generated by the system 100. In general, the display or screen is a computer generated image or series of images capable of being viewed by a person when presented on a device. The display is generally graphically rendered and presented to a device operator on a display device unit (e.g., a television screen, a computer monitor, or a mobile device electronic display) of the device.

The underlying operations that may be used to generate the displays of FIGS. 8-33 may be performed by the operator device 102, the benefit management device 106, or the plan design device 108; partially by the operator device 102, the benefit management device 106, and/or the plan design device 108; or may be otherwise performed. The displays shows in FIGS. 8-33 may provide visual information regarding a rebate model.

Figure 8:
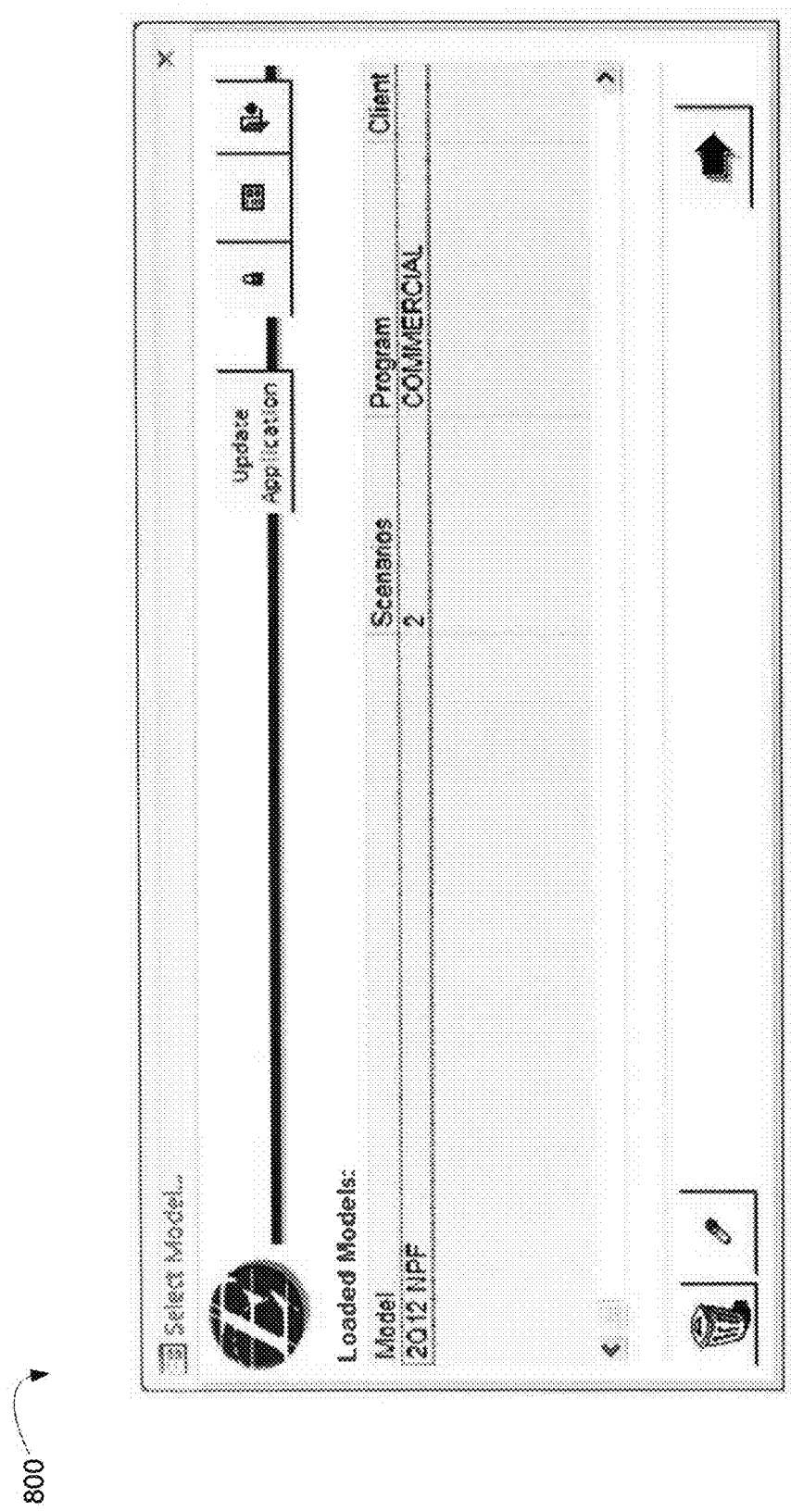

FIG. 8 illustrates a display 800 at which a user (e.g., a device operator) may select a model. The display 800 may include a list of loaded models. Models might be categorized according to plan sponsor, according to the purpose for which the model was created (e.g., training, marketing, etc.), according to the program (e.g., commercial, Medicaid or Medicare), and/or may be otherwise categorized. In an embodiment, an operator device 102, a benefit management device 106 and/or a plan design device 108 generates the display 800 and performs the functionality to allow a user to select a model for a specific client at an operator device 102 to access the client data 112, the drug data 114, and/or the rebate data 118.

In some embodiments, the display 800 may include an update model button. The update model may enable the underlying model to be updated without changing the plan sponsor data.

Figure 9:
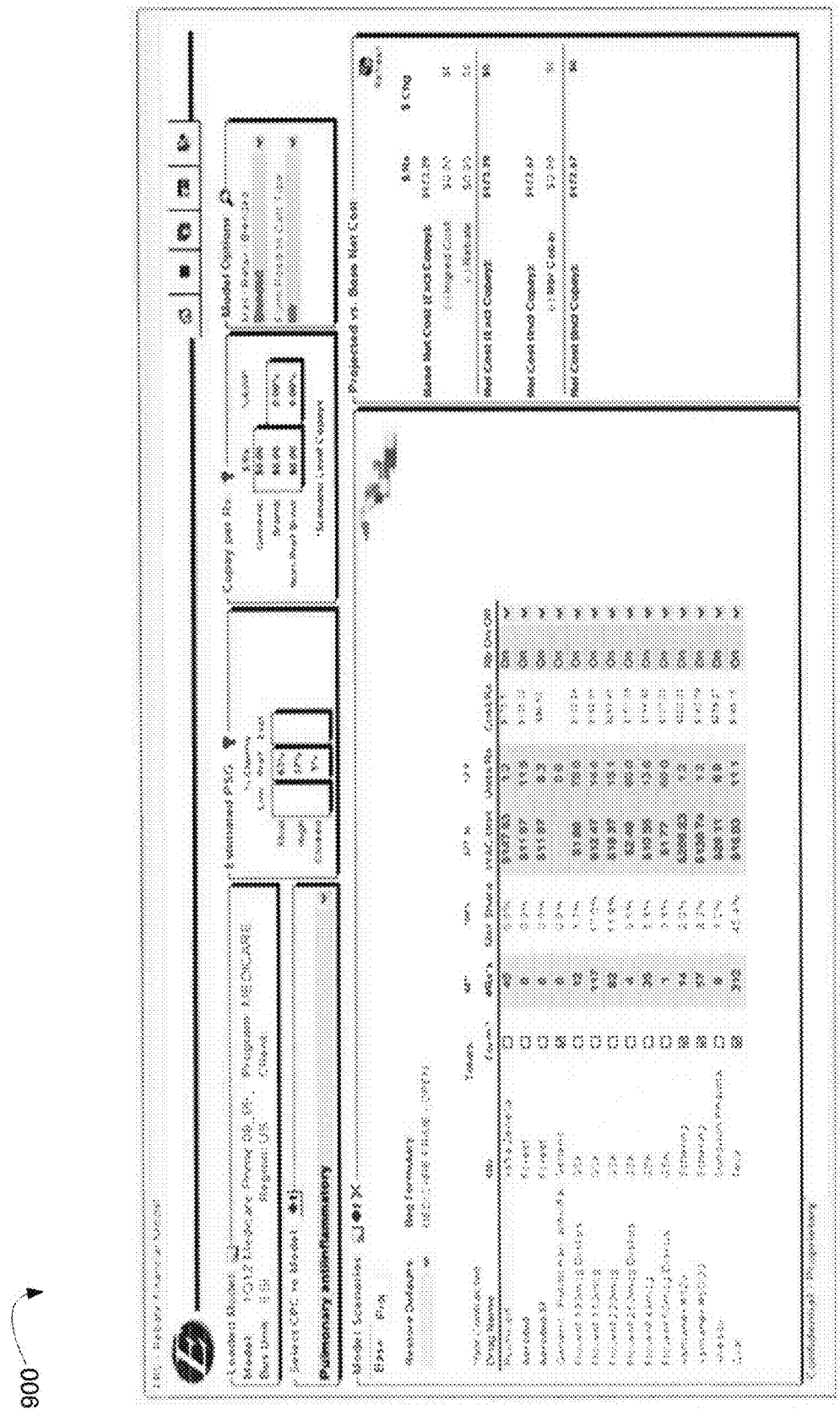

FIG. 9 includes a model scenario portion of a display that may include a list or other indicator of available scenarios. The model may default to a single base scenario when initially loaded, as shown in the display 900. Scenarios may be added or may be otherwise provided. In the example of the display 900, selecting the + button next to the model scenarios header of display 900 activates a scenario functionality that allows addition of scenario(s). A user may define the scenario. In some embodiments, a user may add up to 4 additional scenarios, excluding the base. Other quantities of scenarios may be accommodated in other embodiments.

After selecting the + button next to the model in the display 900, the user selects a type of utilization. Examples of utilization include mail utilization, retail utilization, or a blended mail and retail utilization. Such characterization may affect the utilization data accessed at block 604 or block 704 (see FIGS. 6 and 7).

Figure 10:
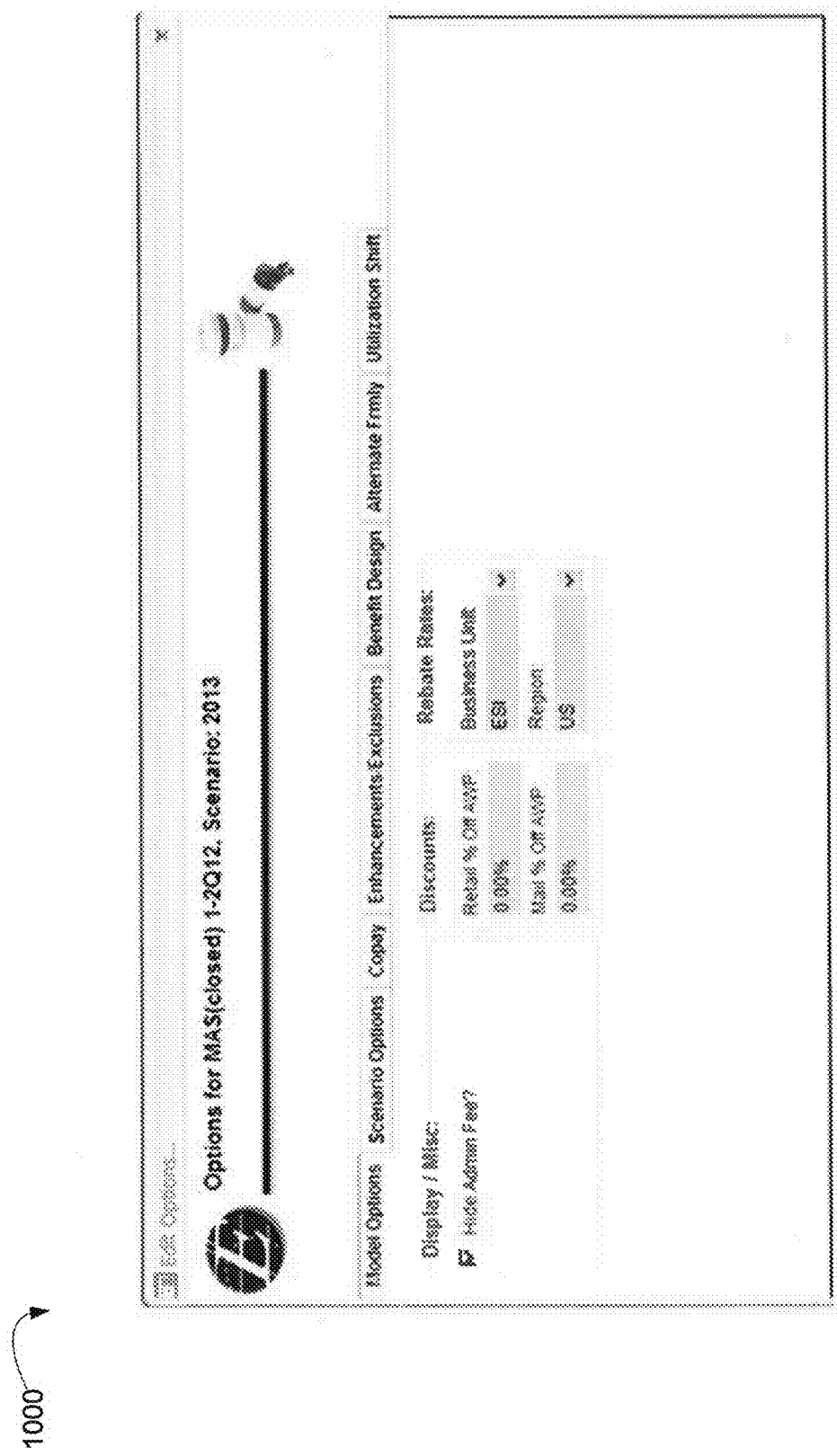

The user may then be provided with a model options tab as shown in display 1000 of FIG. 10. The user may then input client specific options that apply all scenarios across the entire model. One option includes set AWP discounts for retail and mail. In some embodiments, the AWP discounts may be used when calculating ingredient costs. Business units and regions (e.g., Puerto Rico and the United States) may have specific rates that are separately called out in the rebate model.

Figure 11:
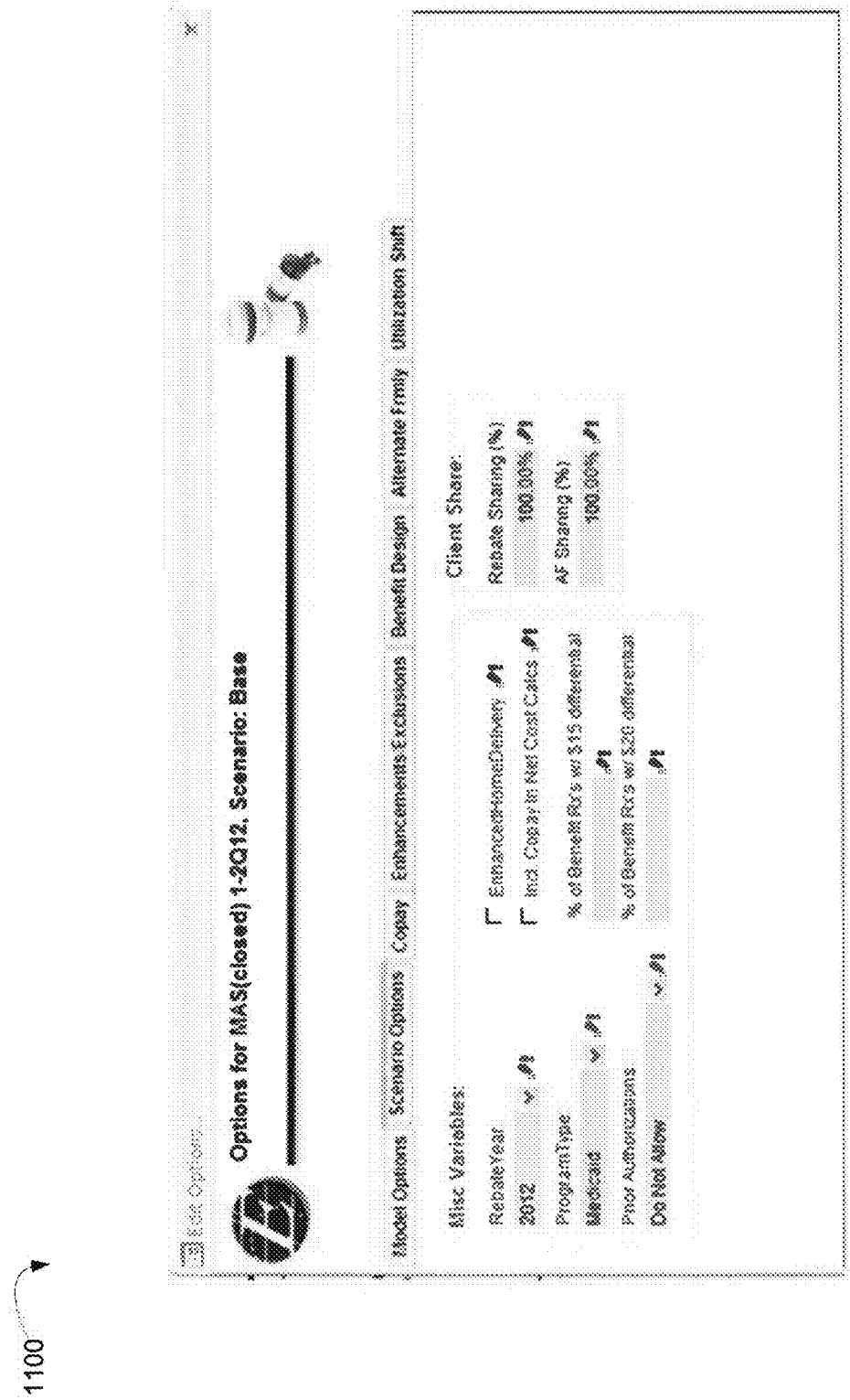

When the scenario tab is selected, the user may then be provided with scenario information as shown in display 1100 of FIG. 11. The user will choose options in the display 1100 specific to this scenario. However, by selection of a button the settings can be applied to all scenarios across the rebate model. The user may set the rebate year, program type, prior authorization setup, plan sponsor contract arrangements and various other settings to accurately reflect the plan sponsor setup through interfacing with the display 1100.

Figure 12:
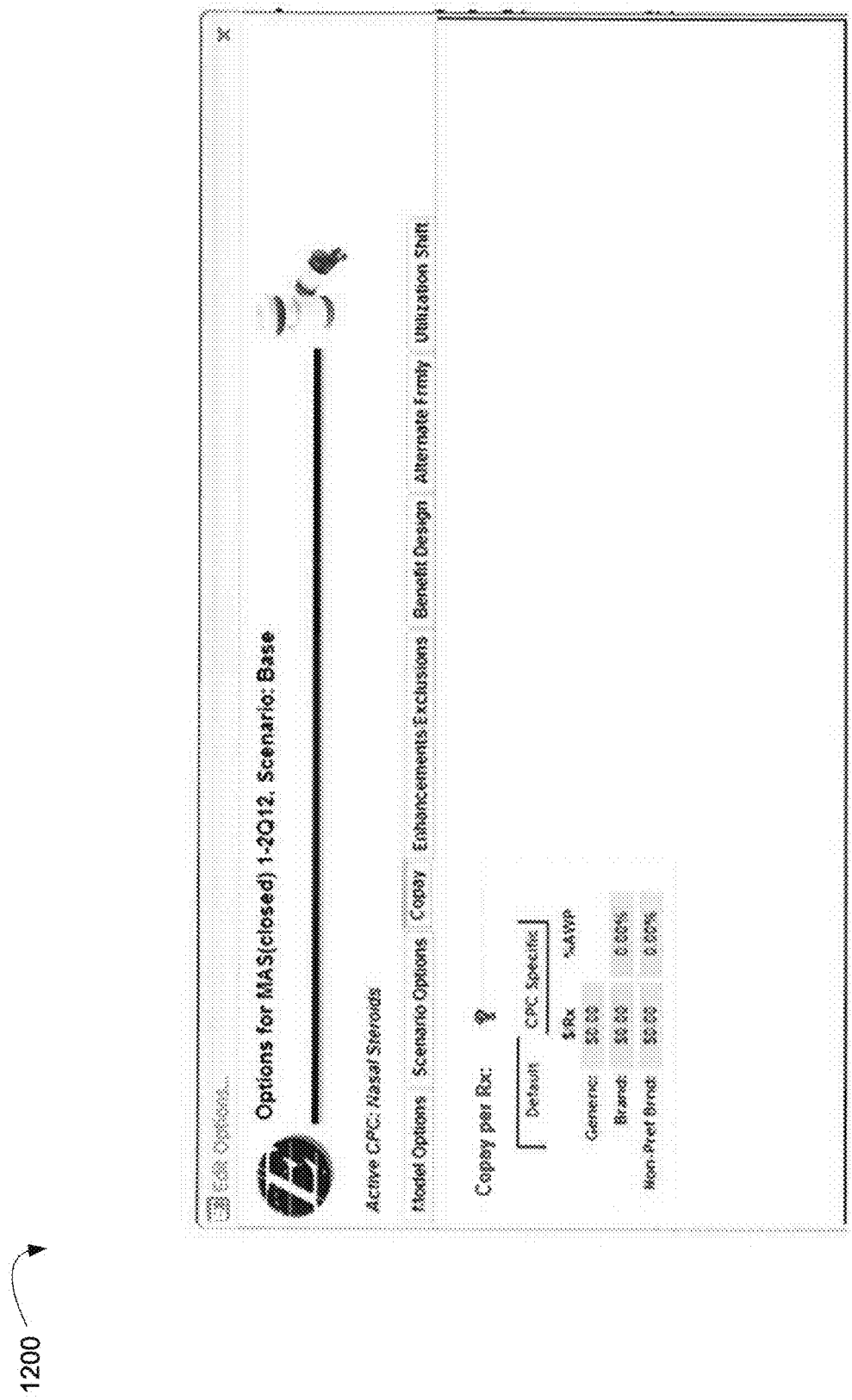

When the copay tab is selected, the user may then be provided with copay information as shown in display 1200 of FIG. 12. The copay structure, identified as a per Rx basis or percentage of AWP is shown in the display 1200. The user may set the generic, brand, and non-preferred brand copays depending on the plan sponsor setup. These settings can apply to the plan sponsor as a whole or on a drug classification by drug classification basis.

Figure 13:
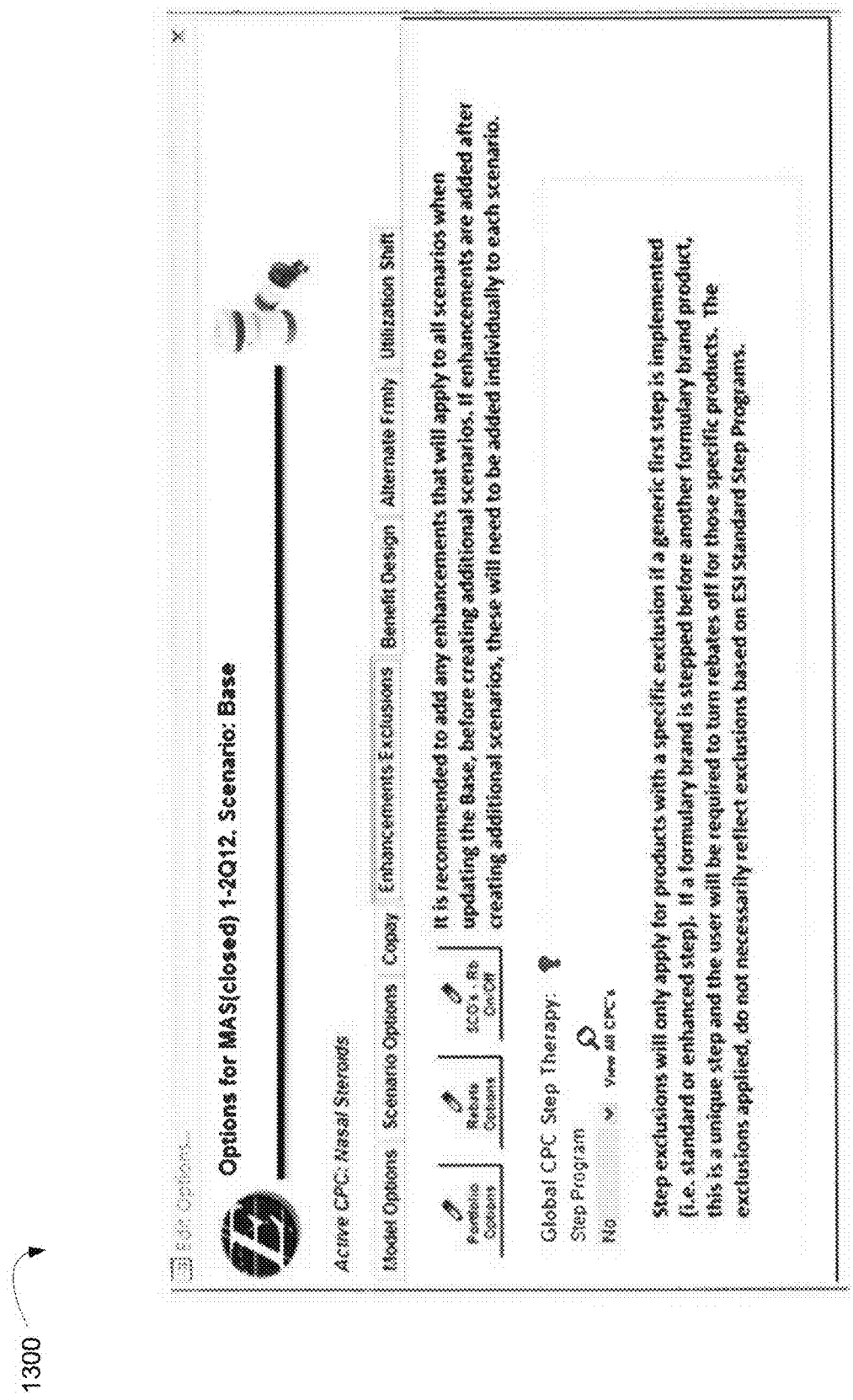

When the enhancements/exclusions tab is selected, the user may then be provided with enhancements/exclusions information as shown in display 1300 of FIG. 13. The enhancements and exclusions included in the display 1300 is where rates with additional parameters can be turned on and off. Plan sponsor based options may be automatically turned on when the rebate model is loaded. In addition, exclusions may be applied and rates pushed to specific cells in the grid by utilizing the step therapy program drop-down as some drugs lose rebates based on these step therapy programs.

Any changes to these settings can apply to the plan sponsor as a whole or on a drug classification by drug classification basis.

Figure 14:
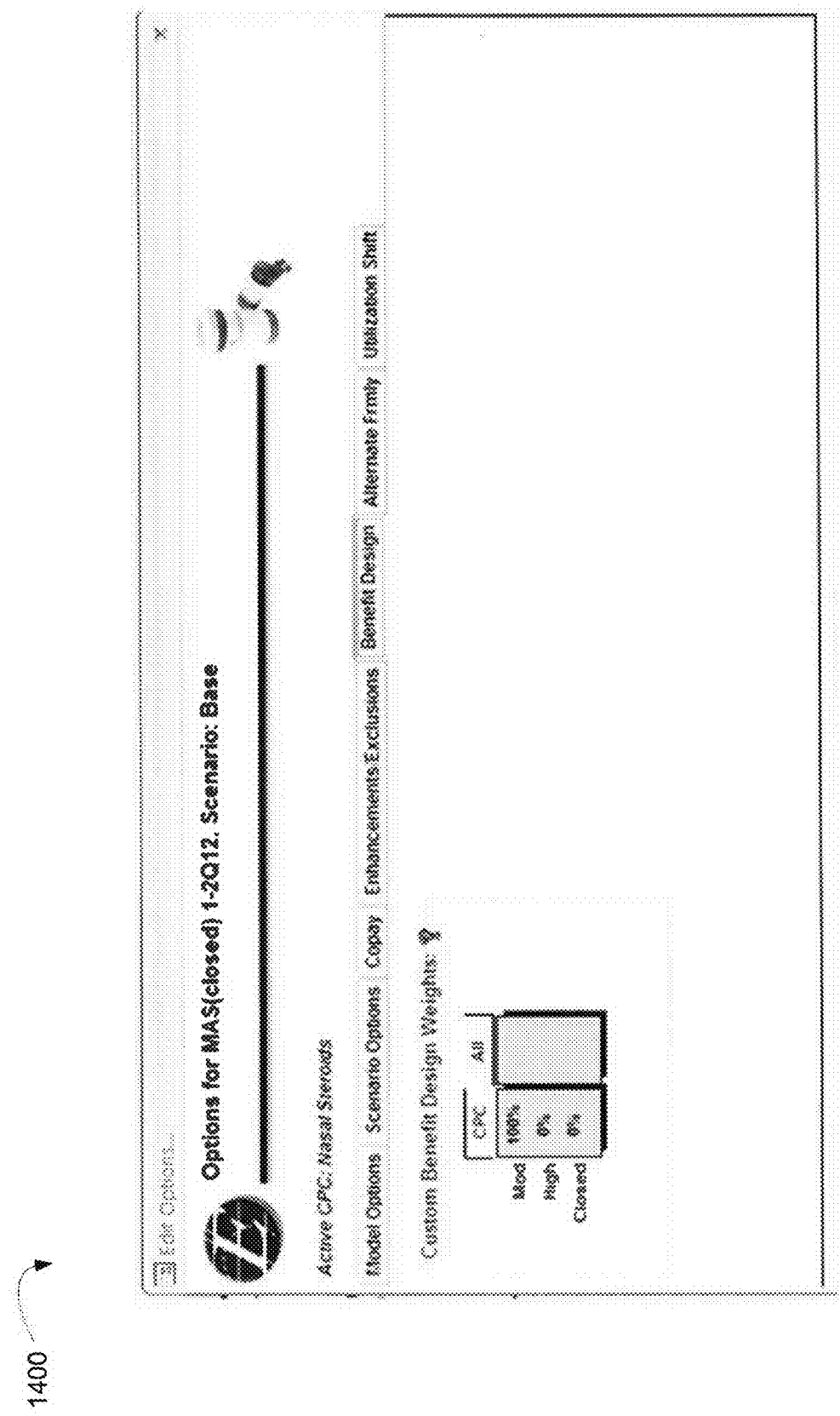

When the benefit design tab is selected, the user may then be provided with benefit design information as shown in the display 1400 of FIG. 14. Benefit design shown in the display 1400 is derived based on the utilization, if available, but may be modified by the user, what-ifs or known changes the plan sponsor will be instituting. The benefit design defined through interfacing with the display 1400, in some embodiments, is one of the two factors in determining what cell of the grid a claim hits. Any changes to these settings can apply to the plan sponsor as a whole or on a drug classification by drug classification basis.

Figure 15:
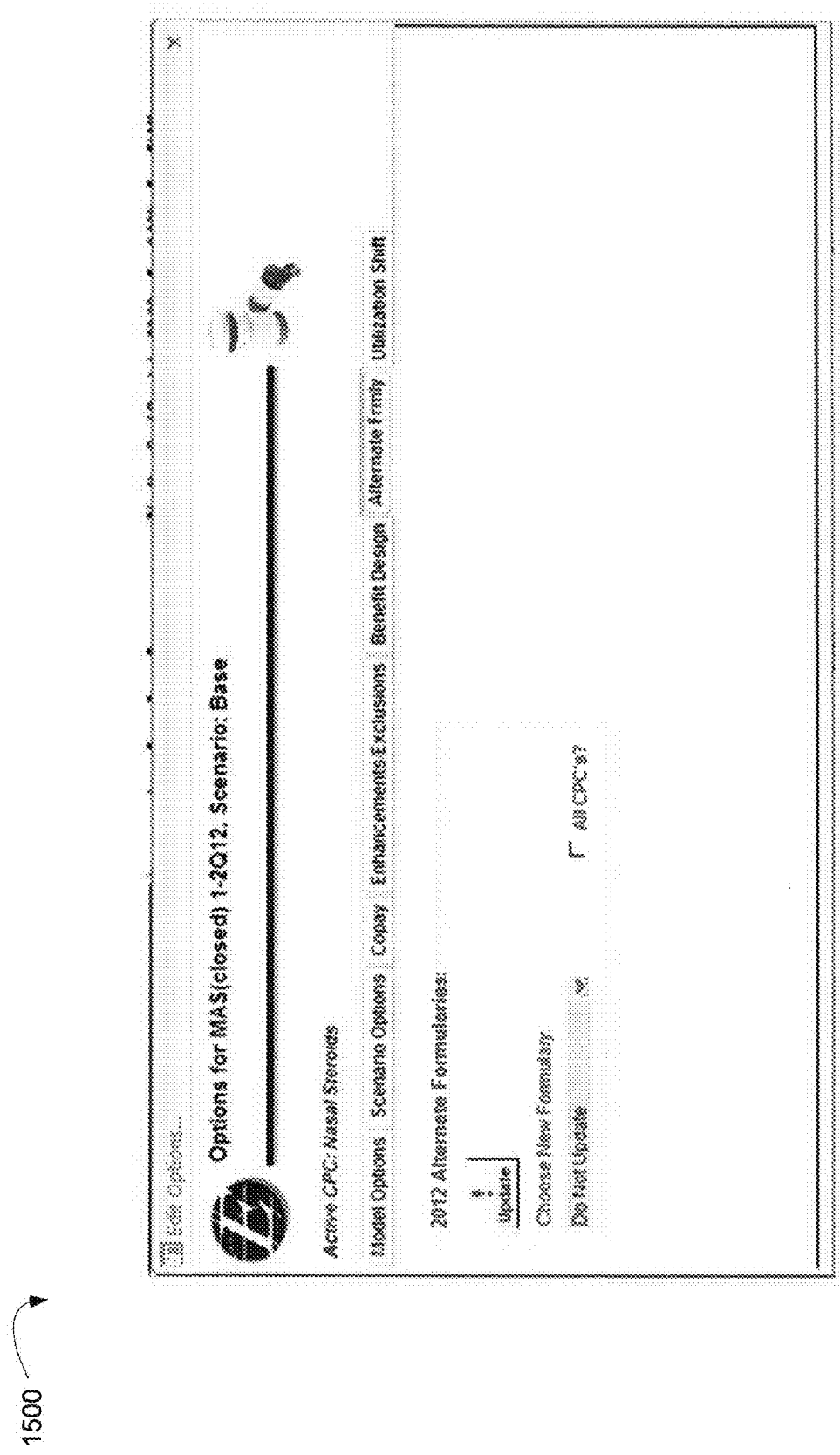

When the alternate formulary tab is selected, the user may then be provided with formulary information as shown in the display 1500 of FIG. 15. For a scenario, a user may opt to select an alternate formulary that will be in place (e.g., for the following year). Any changes to these settings can apply to the plan sponsor as a whole or on a drug classification by drug classification basis.

Figure 16:
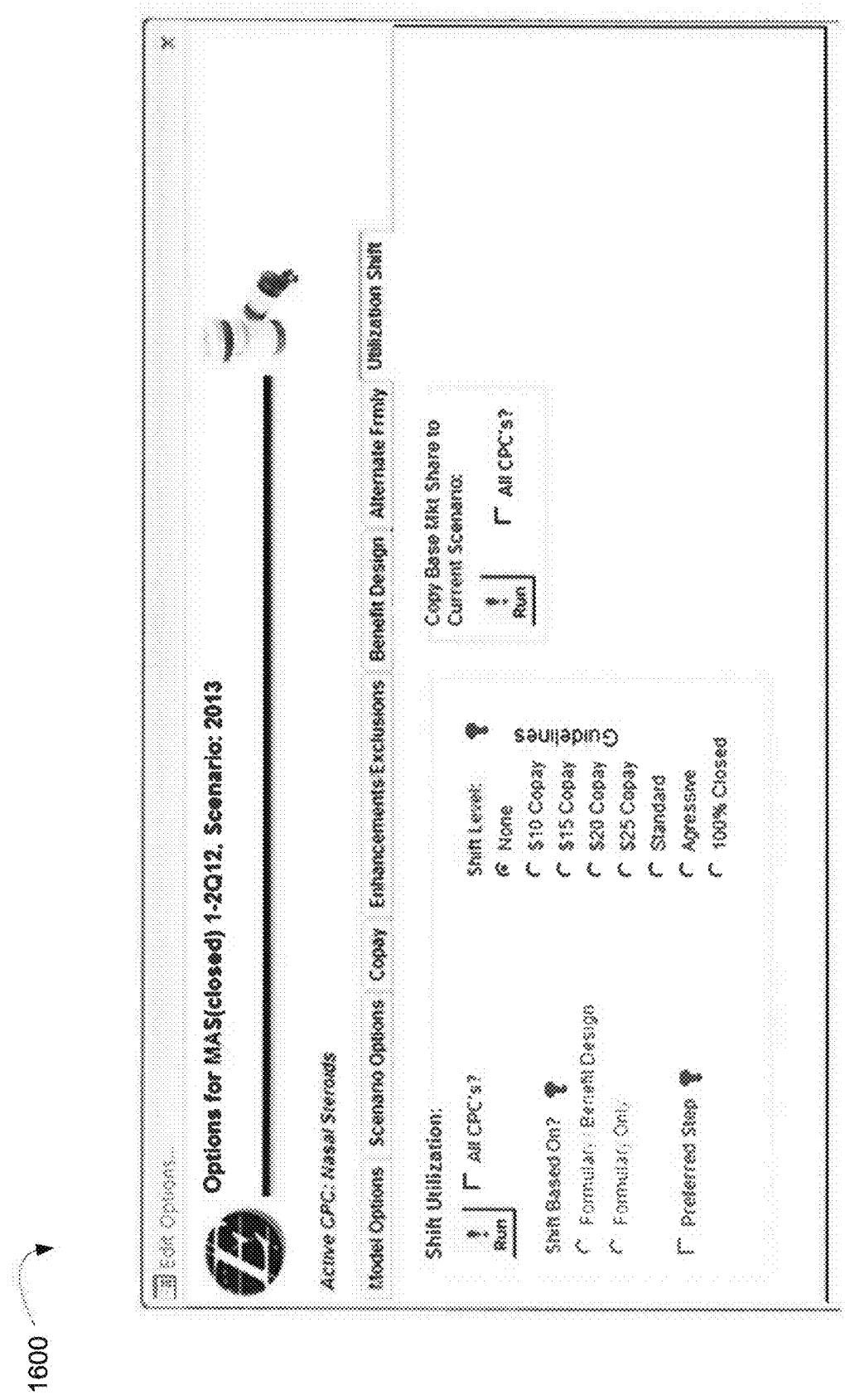

When the utilization shift tab is selected, the user may then be provided with utilization shift information as shown in the display 1600 of FIG. 16. The user may interface with the display 1600 to automatically shift market share based on pre-defined business assumptions. After closing the model options form, the rebate model will update based on the new settings, and may generate and display a main screen as an updated version of the display 900. The user may also opt to manually shift market share on the main screen.

In the model scenario section (drug detail) of the display 900, additional scenarios may be added for comparison purposes. A quick view of the drug classification financial impact is available on the right margin of the display 900. The user may also able to add or remove products from formulary based on the scenarios the plan sponsor opts to model.

The user may then populate reporting as well as prepare for a presentation to the plan sponsor. In some embodiments, the modifications to the various models may be iterative.

The top of the main screen of the display 900 may include a button to compile reporting. After selecting this button, the user will be presented with a display to choose the model, two (or more) comparison scenarios (e.g. base and projected), as well as enter dates for patent projection start date, rebate year over year (YOY) percentage increase and annual inflation rate. The user may then selection a button to compile (e.g., the reports).

Figure 17:
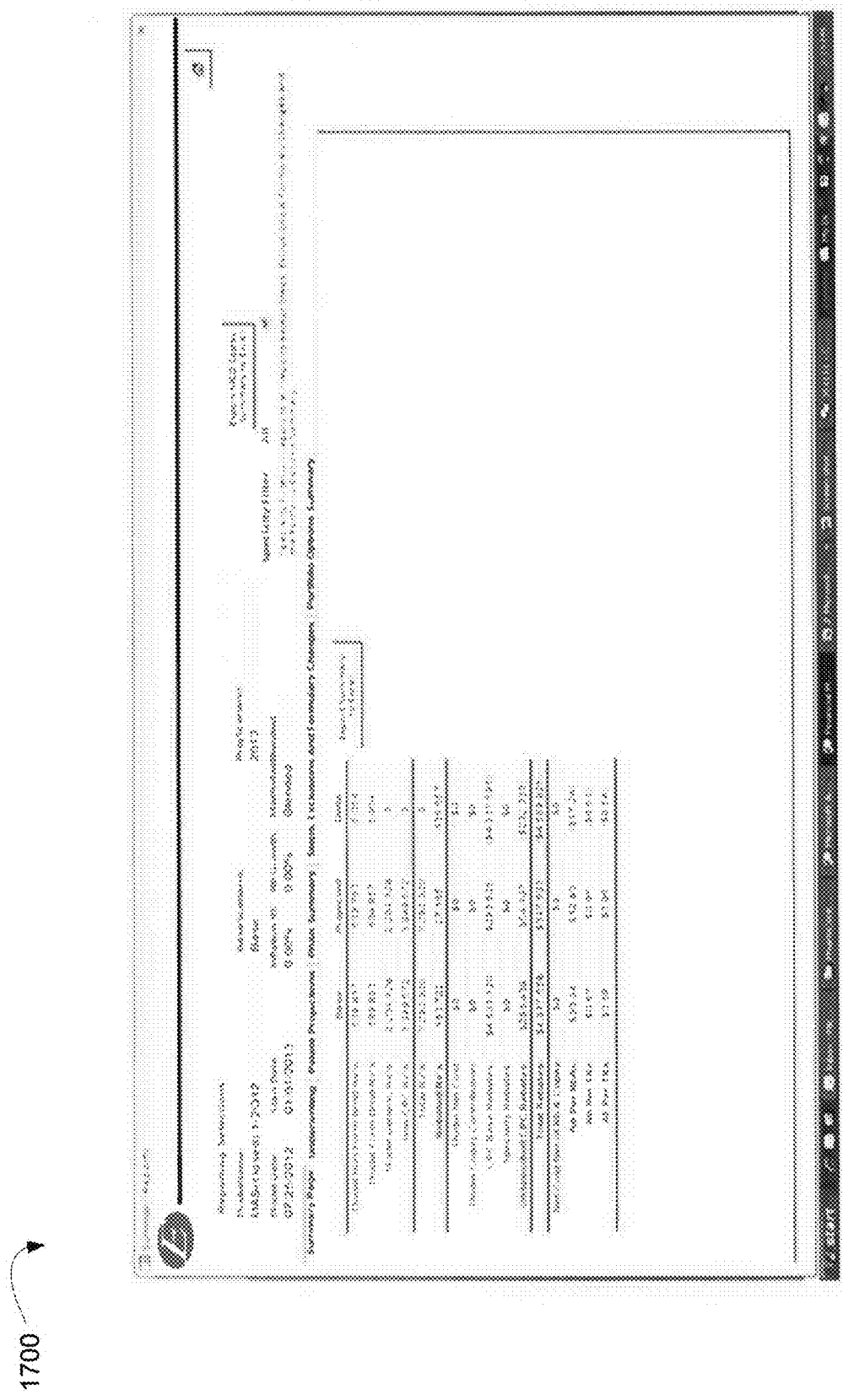

Upon completion of compiling reports, a report as shown in the display 1700 of FIG. 17 may open with a summary. By selection of additional tabs, the drug classification detail as shown in the display 1800 of FIG. 18 and a multi-year projection as shown in the display 1900 of FIG. 19 may be displayed. This display 1700 may also include features to export reports, for further analysis and plan sponsor presentation.

Figure 18:
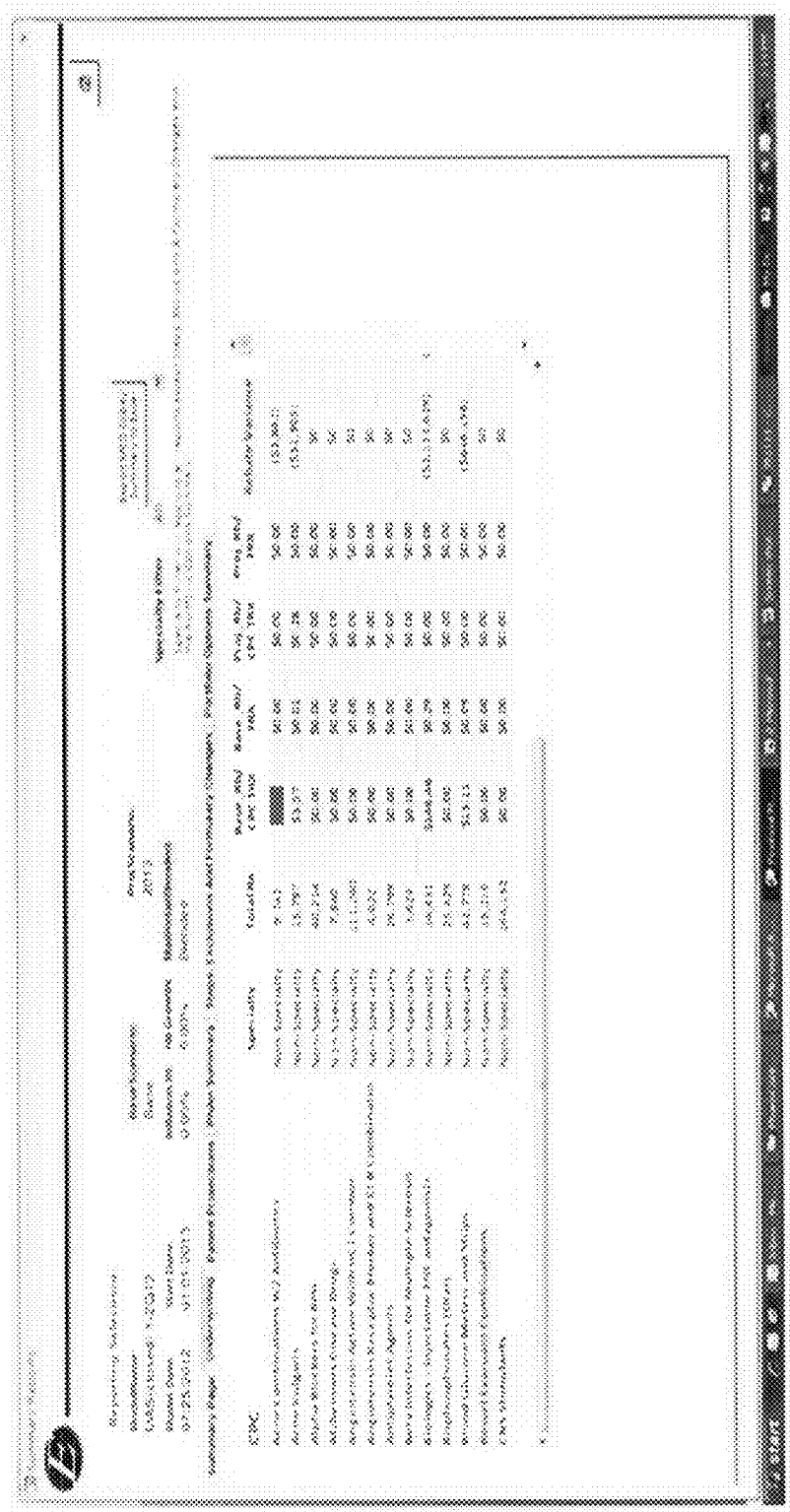
Figure 19:
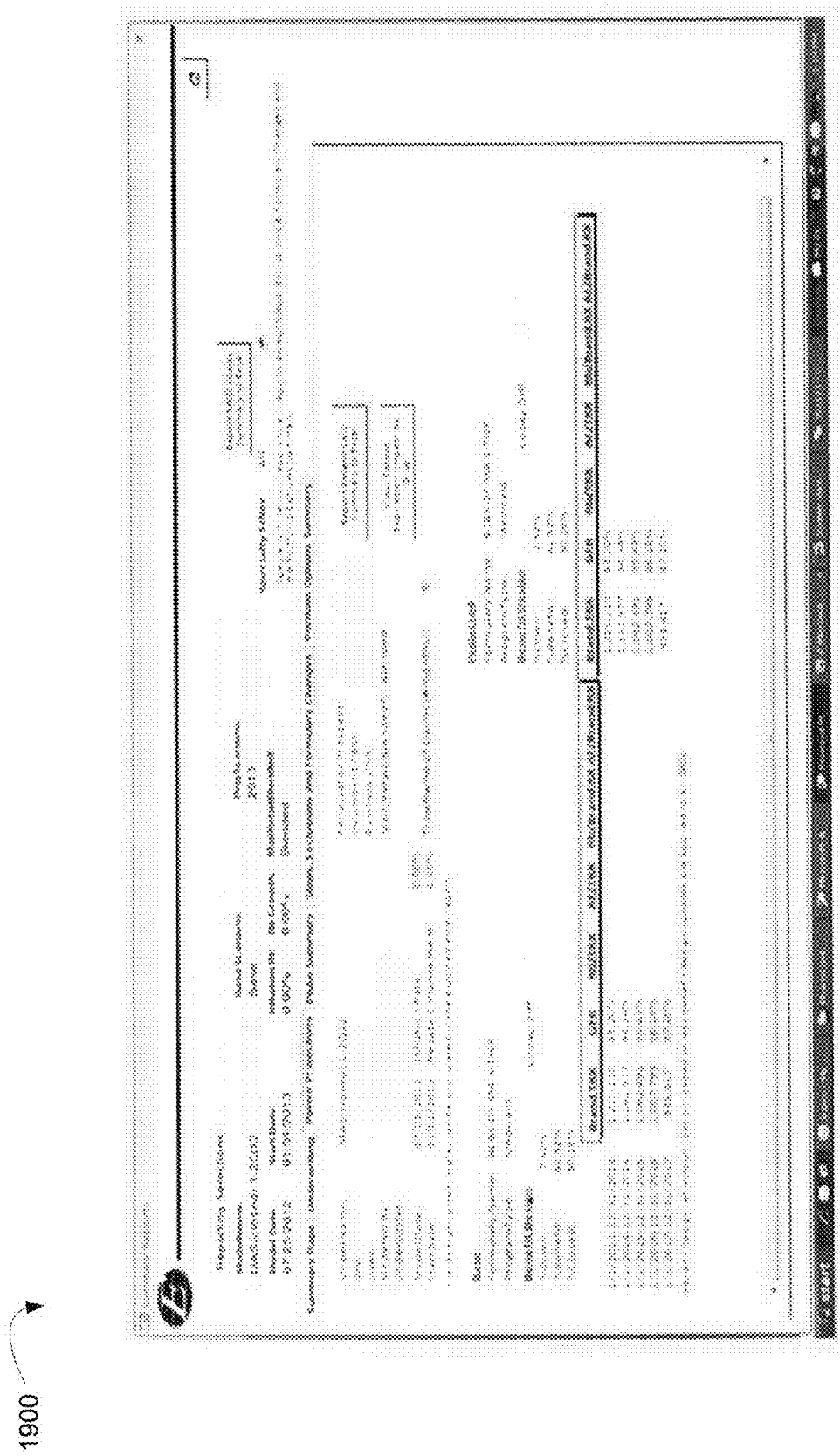

The display 1800 in FIG. 18 shows an example of an underwriting tab, while the display 1900 in FIG. 19 shows an example of an example of a patent projections tab.

FIGS. 20-24 illustrate various features of displays 2000, 2100, 2200, 2300, 2400 an example in which a user may select a scenario, input data, view information, select among modeling options, and/or otherwise engage functionalities. In some embodiments, a listing of scenarios is displayed as a set of tabs on a display, such as display 2000. A user may select a scenario by selecting the tab that lists that scenario.

Figure 20:
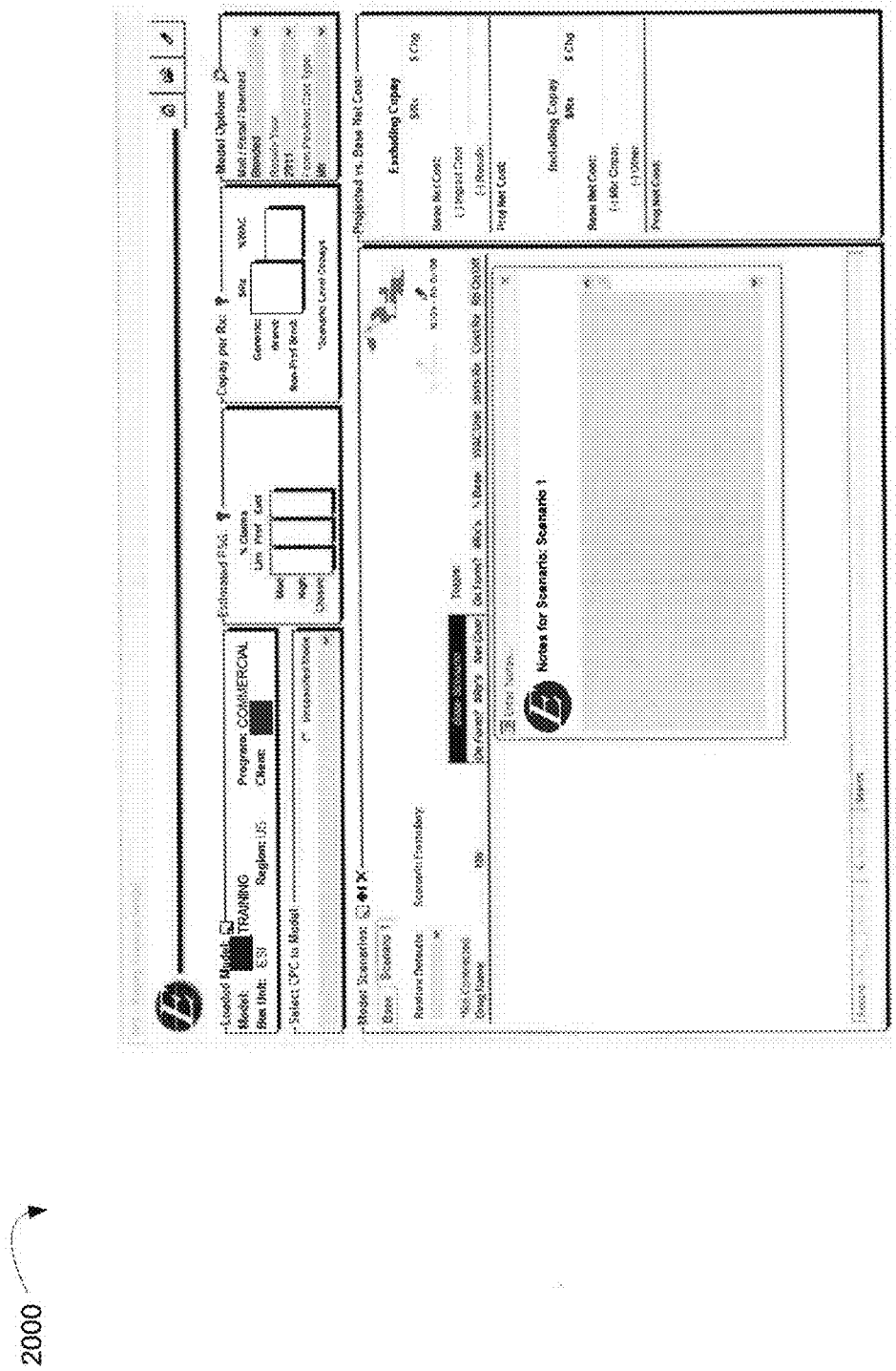

At a display 2000, a user may add notes to the scenario (e.g., via a notepad displayed when a user selects a notepad icon, as illustrated on FIG. 20) or delete a scenario (e.g., by selecting an X).

Figure 21:
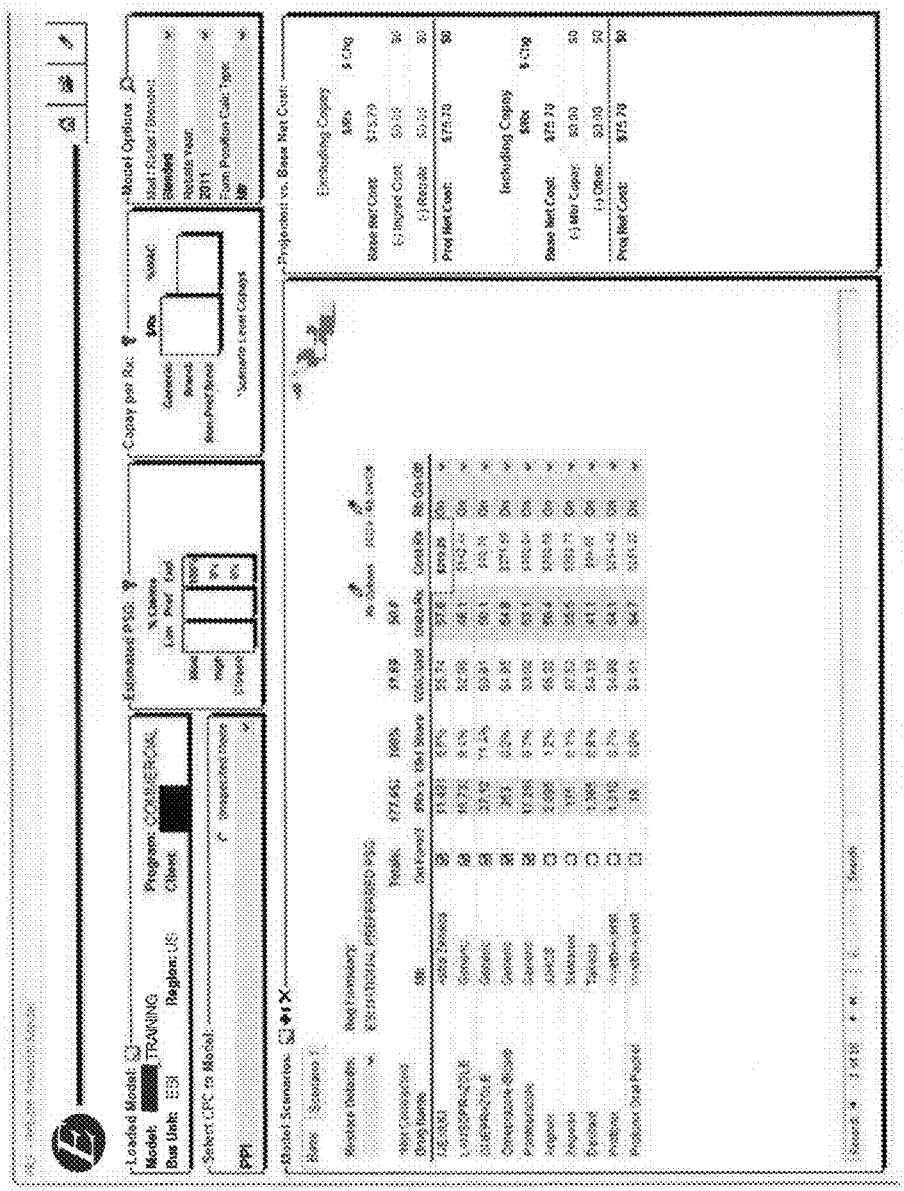

Formulary design options, and the effect of formulary changes on a plan sponsor's cost and/or the guaranteed rebate, may be illustrated by drug class. In the displays 2100, 2200 illustrated in FIGS. 21 and 22, the drug class (abbreviated as CPC) of proton pump inhibitors (abbreviated as PPI) has been selected by selecting PPI from a list displayed when a drop down menu is engaged. FIG. 21 includes an illustration of a display 2100 after a base scenario has been selected that is populated with information about drugs in the selected drug class.

An unspecified drug class may refer to a group of drugs that have been identified as unique. A portion of a display 2100 allows a user to select such group of drugs by selecting "unspecified mode." In an example embodiment, identification of comparable drugs to an unspecified drug may be made available.

In some embodiments, a user may view drugs within a drug class, e.g., to allow a user to compare net cost. Thus, a user may view both the financial impact of rebate and/or rebate guarantee changes (which apply most often to brand drugs) and the cost differential between brand and generic drugs to determine, for example, if a formulary position/plan design that emphasizes rebates may have a negative financial impact if discouraging the use of what might be a lower cost generic drug option.

Method and systems may include dynamic drug classes. For example, changes to a drug class based on factors such as client preferences, product innovation, and the like may be readily accommodated and/or facilitated.

Methods and systems may be adapted to automatically remove a product from formulary and/or update its rebate status based upon its patent expiration date. In this example, a user may more accurately reflect the rebate impact of removing a product from formulary thus potentially generating a more restrictive formulary position within the therapy class. Specifically, the rebate calculation for the guarantee may be adjusted to account for this formulary change.

In some embodiments, guaranteed rebates are projected over a number of years, and patent expirations are factored into the projected rebates. For example, a 3 year projection may illustrate how a client's rebates may be affected, how generic fill rate may change, and may otherwise summarize the impact of patent expiration on pharmaceutical benefit plan design. In one embodiment, the impact of anticipated patent expirations is pro-rated over time to determine a client specific rebate guarantee. In another embodiment, guarantees are adjusted after patent expiration; in this example, the system and method facilitates removal of the impact of patent expirations in calculating rebate guarantees but still takes into account rebate enhancements and inflation.

In the example displays of FIGS. 20-23, the base scenario includes only the starting (base) data. Providing a default base facilitates illustration of the financial impact of formulary changes and/or other plan design decisions. Each scenario defaults to the BASE. A Projected vs. Base Net Cost portion of displays 2100, 2200, 2300 further facilitates illustration of the financial impact of pharmaceutical benefit plan design decisions. In the embodiment of FIG. 21 which illustrates a display 2100 depicting a Base scenario, the Projected vs. Base Net Cost portion of the display 2100 shows no change.

In displays 2100, 2200, 2300 the items in columns labeled On Form?, WAC/Unit, and Units/RX can be updated by a user. In some embodiments, a user can adjust the market share (e.g., percentage share of the drug in its class, as illustrated under the heading Mkt Share in display 2100) based on formulary, patent expirations, and/or benefit changes.

A portion of displays 2100, 2200, 2300 may allow a user to input data representing the co-pay per prescription and/or such portion may display co-pay per prescription based on client data or otherwise. The amount of a co-pay typically does not affect the amount of a rebate, but will have a financial impact on the client's overall cost and, therefore, may be useful in connection with pharmaceutical benefit plan design.

In some embodiments, a method may be deployed to determine whether a formulary position is limited, preferred, or exclusive based on manufacturer or individual drugs. A portion of displays 2100, 2200, 2300 (under the heading Form Position Calc Type) may allow a user to select whether calculations will be based on manufacturer or drug. For example, if manufacturer is selected and there are two manufacturers with formulary drugs in a drug class, then the formulary might be classified as preferred. If one or more of those manufacturers produce more than one drug in a drug class, however, then a calculation selection based on drug may characterize formulary position as limited.

The following example illustrates the potential benefits of benefit design at the drug level, as applied to a guaranteed rebate.

Drug Level Benefit Design vs Drug Class Benefit Design
Assume the following rebate rates:
Rebate Rate: Mod=5%
  High=15%
  Closed=25%
Based on drug class, assume the following design weights:
  Mod=10%
    High=80%
    Closed=10%
Based on the above, the average rebate rate would be 15%, calculated as follows:

(Mod Ben Des*Mod Rate)+(High Ben Des*High Rate)+(Closed Ben Des*Closed Rate)

(10%*5%)+(80%*15%)+(10%*25%)=0.5%+12%+ 2.5%=15%

Assuming drug costs $100, rebate is calculated as follows:

Total Rebate at Drug Class Benefit Design: $100*15%=$15

Based on individual drugs, assume the following design weights:
  Mod=8%
    High=75%
    Closed=17%
Based on the above, the average rebate rate would be 15.9%, calculated as follows:

(Mod Ben Des*Mod Rate)+(High Ben Des*High Rate)+(Closed Ben Des*Closed Rate)

(8%*5%)+(75%*15%)+(17%*25%)=0.4%+11.25%+ 4.25%=15.9%

Assuming drug costs $100, rebate is calculated as follows:

Total Rebate: $100*15.9%=$15.90

In this example, the difference between calculating based on individual drug instead of drug class is $0.90 per $100 of drug cost.

Thus, by facilitating benefit design and calculation of rebates at the drug level, a plan sponsor may achieve enhanced financial benefits from a guaranteed rebate program. Thus, if a manufacturer's rebates are very specific, modeling at the drug level allows a user to correctly allocate the performance of rebate dollars in one drug specific based on its market share.

A portion of displays 2100, 2200, 2300 (under the heading Mail/Retail/Blended) allows a user to select from a set of assumptions regarding whether prescriptions are filled at retail, via mail order, or both (e.g., blended) into pharmaceutical benefit plan design decisions.

Figure 22:
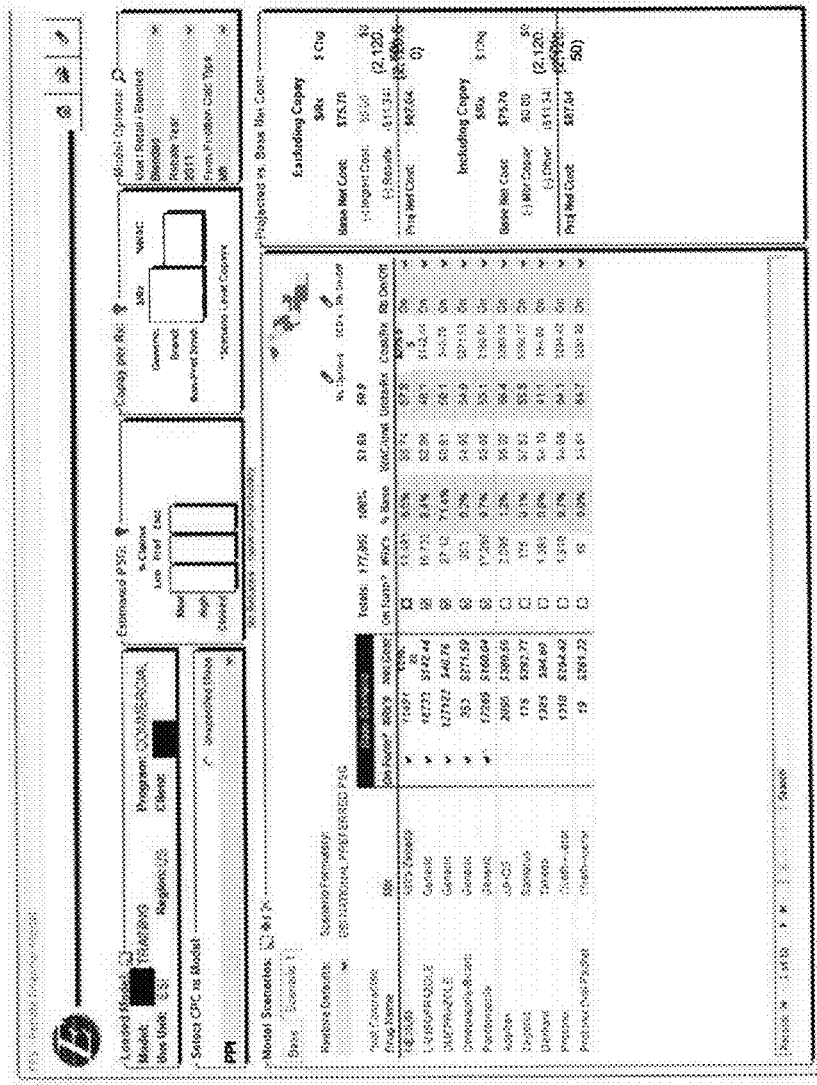
Figure 23:
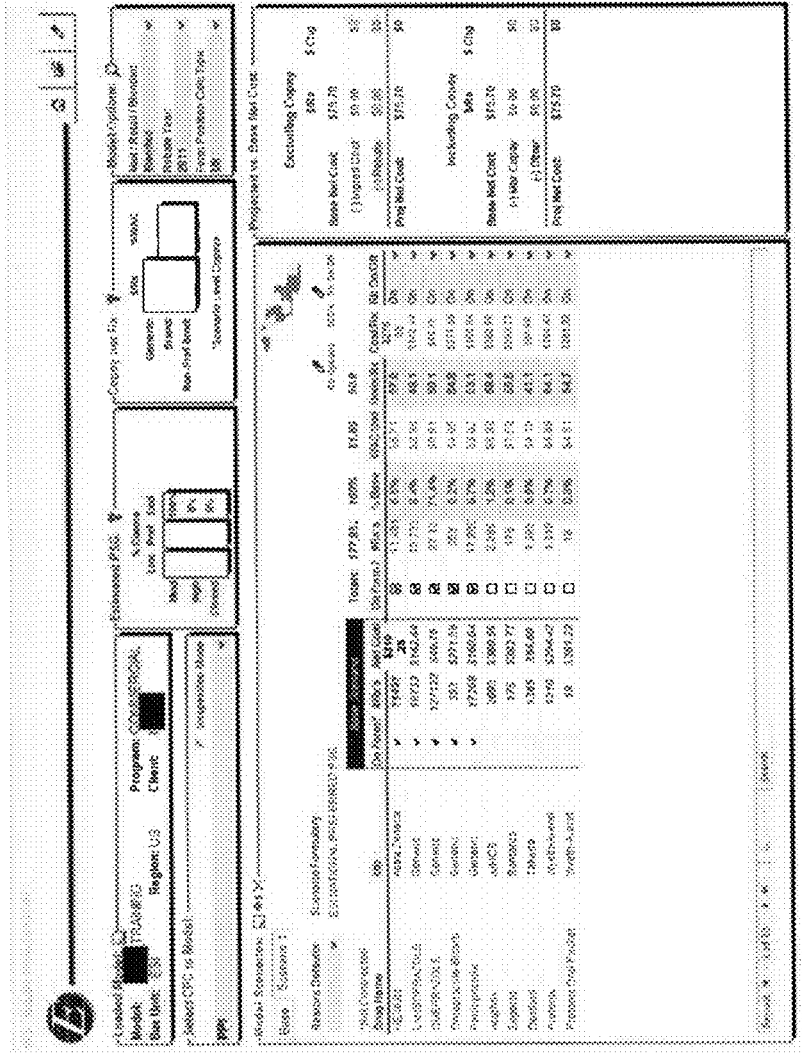

As shown in FIG. 22, a display 2200 provides information about drugs in a selected drug class when a scenario is selected. In display 2200, the Projected vs. Base Net Cost portion illustrates changes to the projected cost caused by changes to the formulary. For example, in display 2200, NEXIUM has been removed from the formulary by unchecking a box under the heading On Form?. Economic changes based on this decision are illustrated in the Projected vs. Base Net Cost portion and in the portion titled Estimated PSG (which shows no rebates for the displayed drug class after NEXIUM is removed, since there are no remaining brand drugs on the formulary).

Information illustrated in displays 2100, 2200, 2300 about the listed drugs may include each drug's name, its manufacturer, an indication of whether the drug is on formulary, the number of prescriptions, the percentage share of each drug in the drug class, the cost per unit (measured, in the example illustrated, by the wholesale acquisition cost or WAC), the number of units per prescription, and the cost per prescription. Other information about a drug and/or its utilization may be included on the displays 2100, 2200, 2300. For example, drugs may be listed separately based on dosage.

In some embodiments, the number of prescriptions (shown under the heading #Rx's) is the actual number of prescriptions filled by a particular plan sponsor's members over a period of time. In an embodiment, the period of time totals approximately six months and is either the first and second calendar quarter or the third and fourth calendar quarter. Use of two calendar quarters may take into account seasonal variations in prescriptions and, therefore, may provide a more accurate predictor of future use than a single quarter. Other time periods, such as a single quarter, alternating calendar quarters, alternating months, consecutive months, or calendar years may be used. Prescription totals may be based on the number of prescriptions filled by one or more entities other than and/or in addition to the client.

A portion of displays 2100, 2200, 2300 may be used to manually override rebate defaults incorporated into rebate data. For example, if a manufacturer has agreed to provide a rebate directly to the client, a user may make a selection under RB On/Off to override any rebates that would otherwise be provided in connection with that particular drug based, for example, on formulary position and benefit co-pay design. In this example, the illustrated projected cost would not include the disabled rebate.

In some embodiments, a user's selection of a rebate as on or off (or other selection that indicates whether or not a rebate is available) may be used to illustrate that a particular aspect of plan design causes forfeiture of a rebate. For example, some manufacturers will deny a rebate for a brand drug if a pharmaceutical benefit plan design requires a step therapy program in connection with that drug. Accordingly, if a plan sponsor has selected step therapy for a drug, noting that the rebate is off may help illustrate the affect of that decision. In one embodiment, the projected cost will illustrate the change in the rebate program based on step therapy regardless of whether the rebate off selection is made—the selection is for illustration purposes only. In another embodiment, the user's selection effects the change in rebate calculation.

As illustrated the embodiment of FIG. 22, when working within one scenario, comparisons to another scenario (such as a base scenario) may be illustrated in a portion of the display 2200. This portion may illustrate, for example, differences in formulary, number of prescriptions, net cost, and the like.

Displays 2100, 2200, 2300 may include a portion that allows a user to engage functionality to restore to a previously-set scenario.

In some embodiments, methods and systems allow a user to add a criteria based enhancement (indicated on displays 2100, 2200, 2300 by Rb Options) or a select client option (indicated on displays 2100, 2200, 2300 by SCOs-Rb On/Off). In an example, changes implemented via a criteria based enhancement and/or select client option may be applied to a single scenario or to multiple scenarios.

Figure 24:
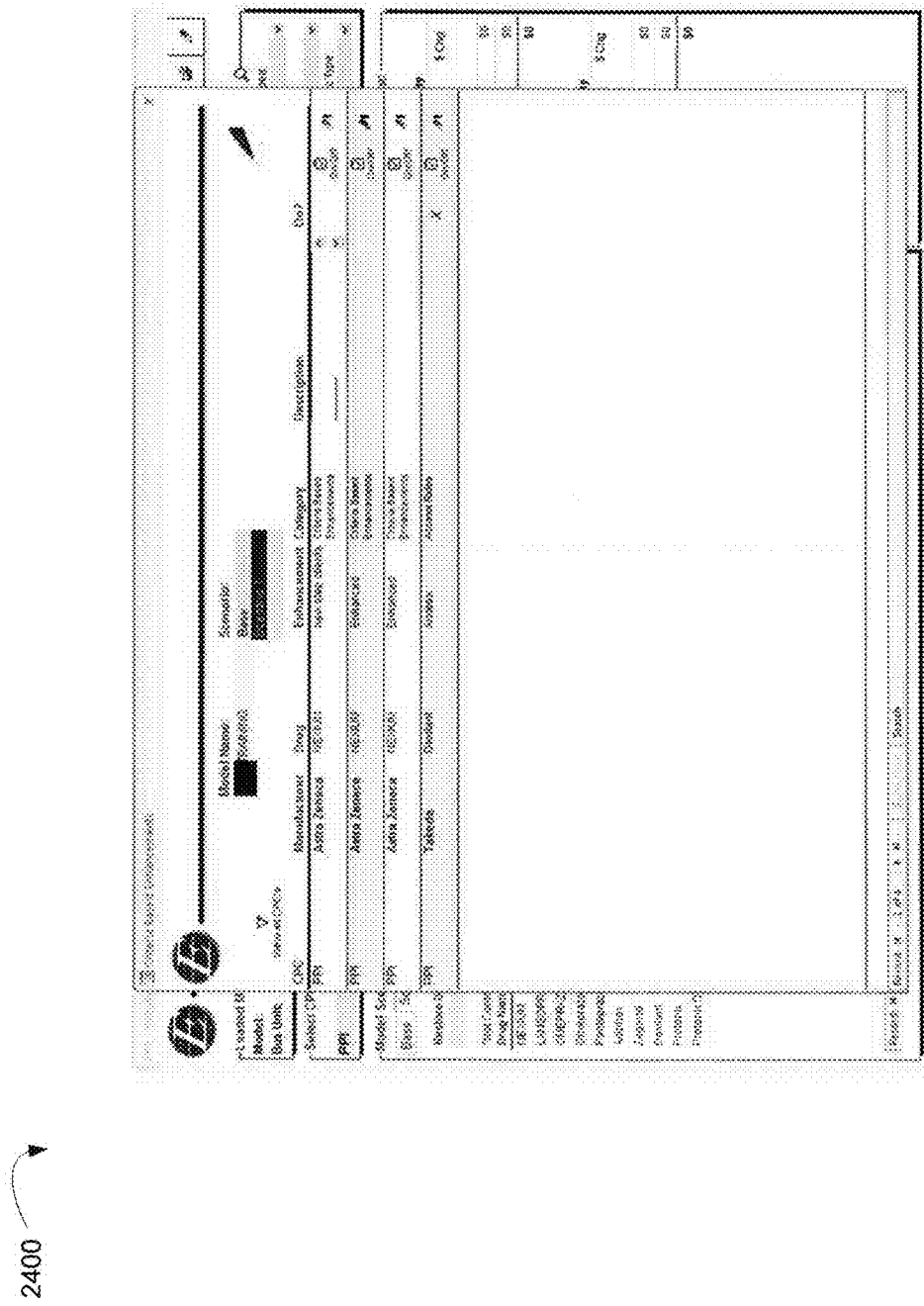

In some embodiments, as illustrated in FIG. 24, selecting a criteria based enhancement may generate a display 2400 that lists enhancements available for particular drugs and allows a user to turn an enhancement on or off. Enhancements may be displayed based on drug class, all available enhancements may be displayed, or another set of enhancements may be displayed. A portion of display 2400 allows a user to direct application of a selected enhancement to all scenarios of the model.

Figure 25:
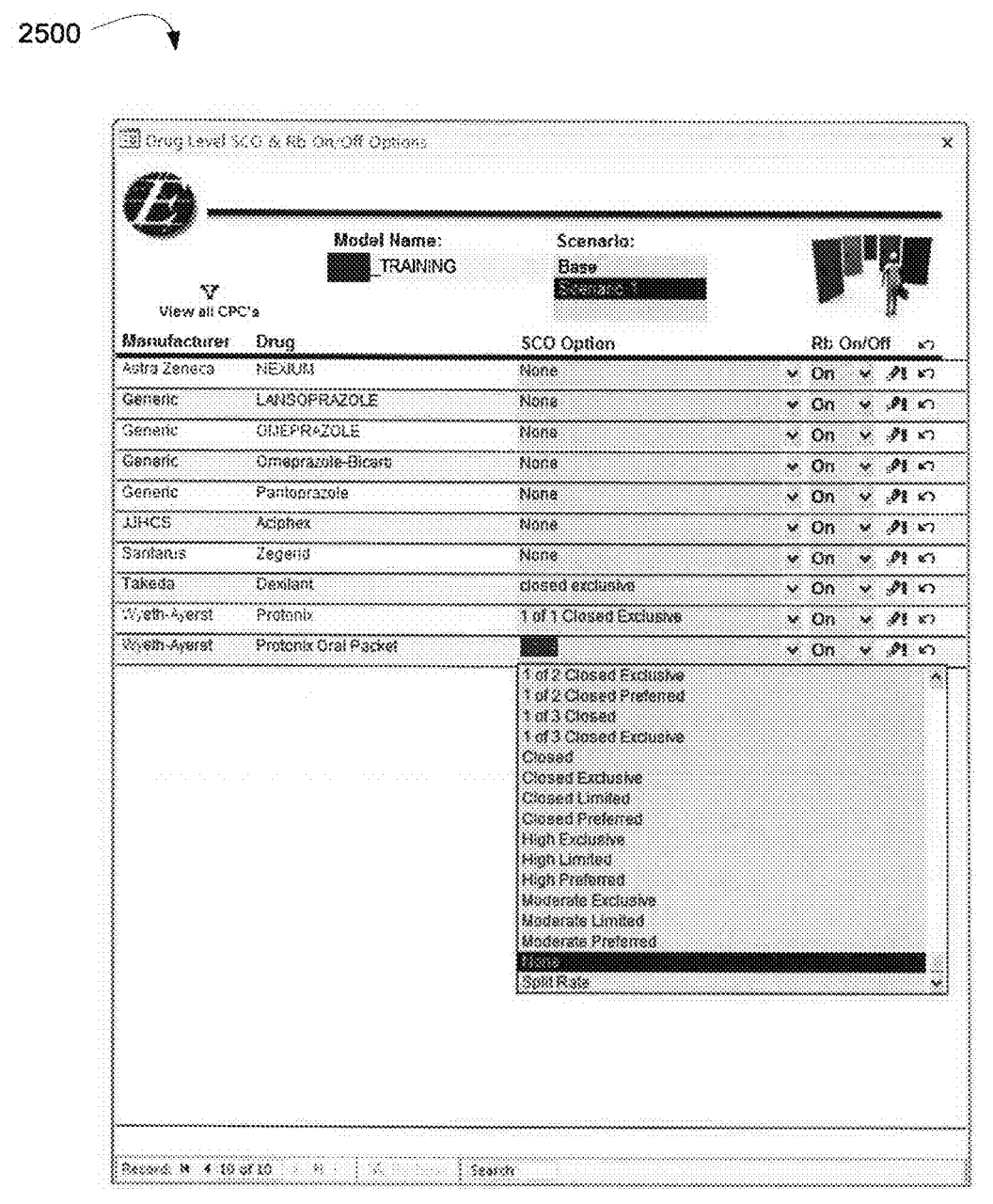

FIG. 25 illustrates an example display 2500 generated upon selection of a select client option. In some embodiments, all available select client options are pre-populated when the model is loaded. A portion of display 2500 includes a drop down menu by which a particular type of rebate can be affirmatively selected for a particular drug; in this example, the rebate type may or may not precisely correspond with the rebate type. Thus, a drug manufacturer may offer a rebate to a particular client as if the formulary position/benefit co-pay design is closed exclusive when it is actually closed limited; a user may select the desired designation. A portion of display 2500 allows a user to direct application of a selected enhancement to all scenarios of the model. Another portion of display 2500 (illustrated by an arrow) allows a user to revert to the default or base option.

In an example embodiment, a criteria based enhancement display 2400 and/or a select client option display 2500 may include functionalities that permit access of a listing of drugs within a drug class for which a criteria based enhancement and/or a select client option may be available or, alternatively, that permits access of drugs across all drug classes for which a criteria based enhancement and/or a select client option may be available. For example, by engaging selection functionalities on displays 2400 and 2500, respectively, a listing of all such drugs may be retrieved.

FIGS. 26 through 32 illustrate displays that may be available when a model option election functionality is engaged. In some embodiments, pharmaceutical benefit plan design selection options may be accessed by selecting the magnifying glass icon next to the Model Options header, e.g., as shown on displays 2100, 2200, 2300.

In some embodiments, an options display will include multiple tabs that represent client specific pharmaceutical benefit plan components.

Figure 26:
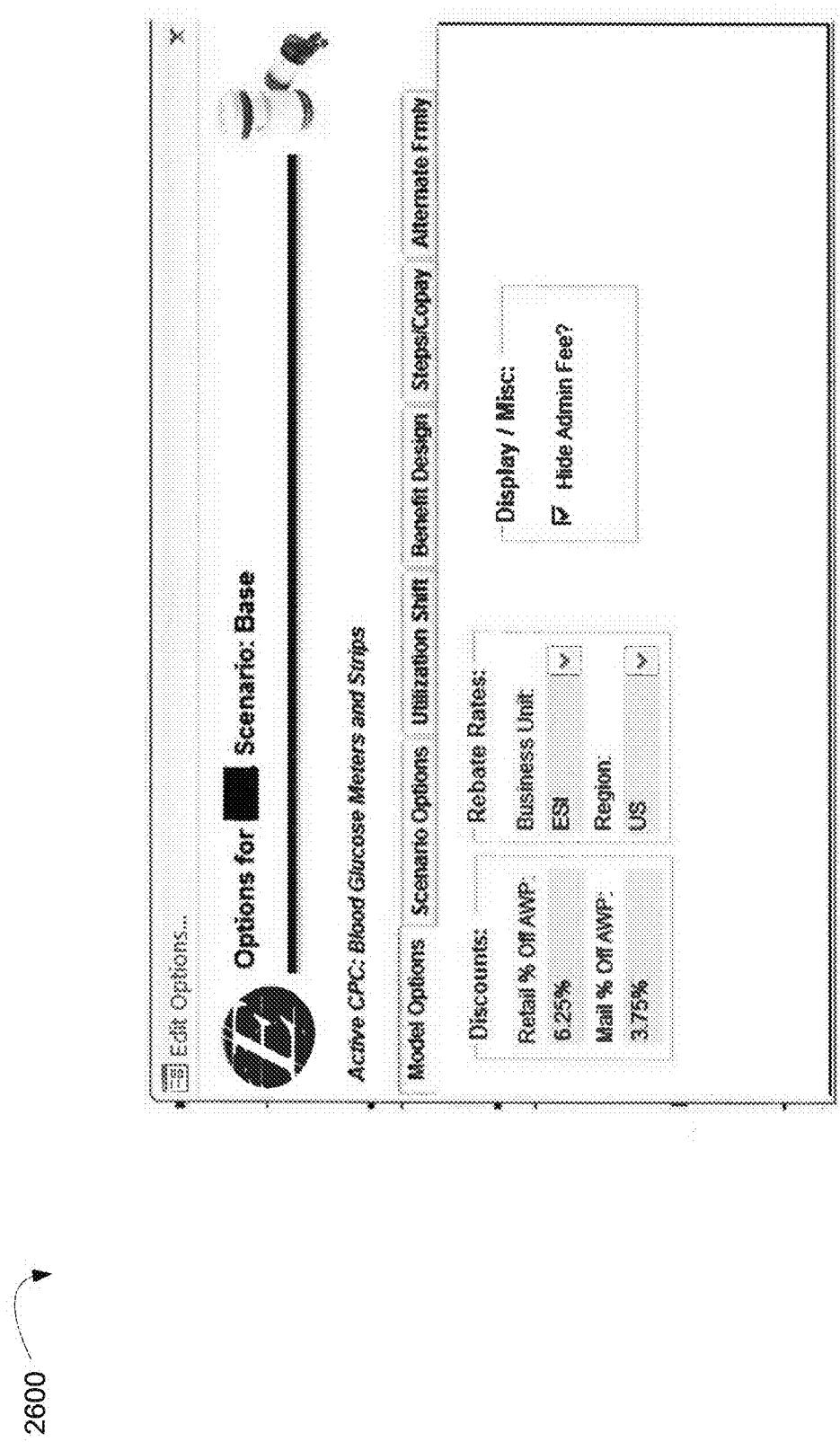

FIG. 26 illustrates a display 2600 produced upon a user's selection of a Model Options tab. This display 2600 includes functionalities that allow a user to choose whether or not the data is to be annualized, an administrative fee can be hidden from display, and the correct rate set can be applied. A business unit (e.g., a business unit within a PBM) can be selected and a region can be selected. In this example, region choices are the United States or could also encompass a country, state, or other jurisdiction or region.

Figure 27:
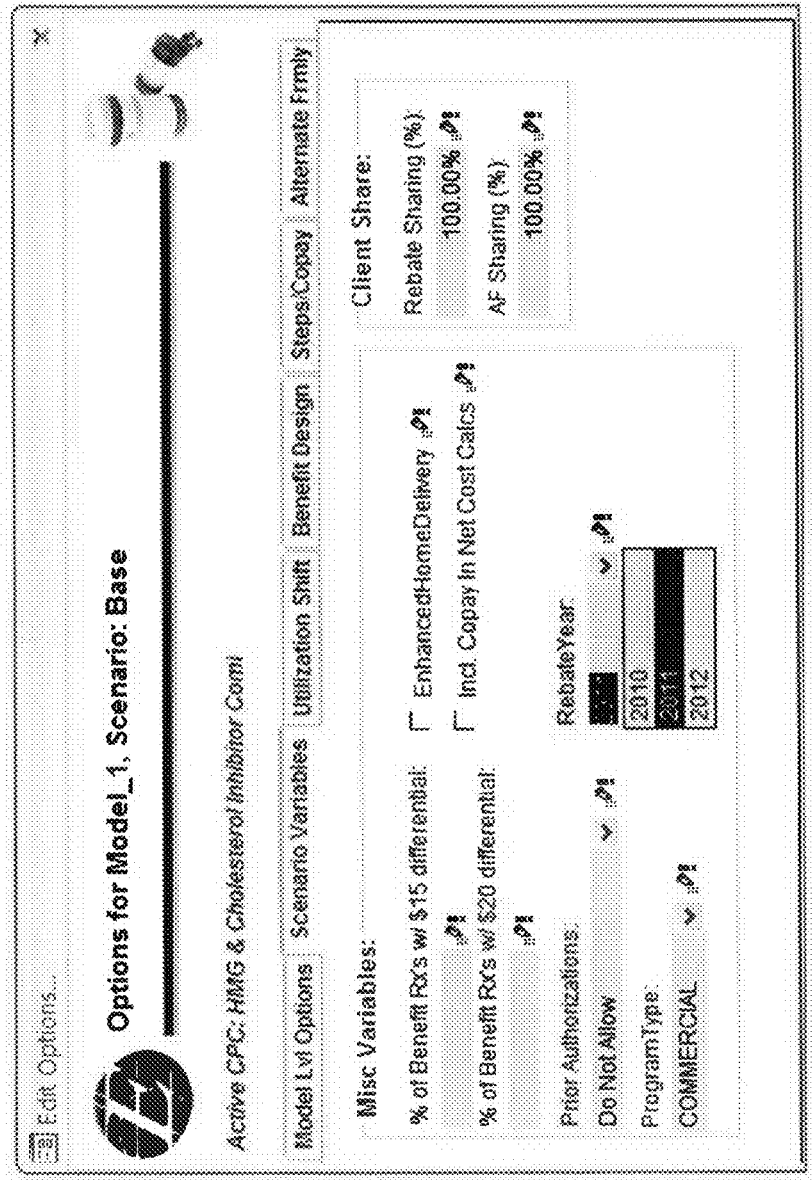

FIG. 27 illustrates a display 2700 produced upon a user's selection of a Scenario Options tab. Some or all of the features selected via display 2700 may be illustrated on a displays 2100, 2200, 2300. An input portion of display 2700 may allow a user to provide a percentage of claims for prescriptions with a least a designated threshold copay differential (e.g., at least a $15 differential, at least a $20 differential, or a selected differential of another appropriate amount).

A user who selects an otherwise closed benefit may enable a prior authorization functionality which, when engaged, permits a member to pay less than 100% of the cost of the drug if the member has a prior authorization in place from their doctor. (A prior authorization may be required under certain health plans and, generally, refers to a requirement that an authorization for a particular prescription drug and/or healthcare service be obtained from the physician before the drug is prescribed and/or the service provided.)

A portion of display 2700 may allow a user to select among types of programs. For example, program types may include commercial, Medicare, and Medicaid. Program selection may affect various aspects of a model, such as drug cost and rebate options.

Portions of display 2700 may allow a user to select a rebate year to analyze the financial impact of a particular plan design (e.g., scenario) in a selected year versus another prior and/or future year. Portions of display 2700 may also allow a user to select a client's rebate share.

Figure 28:
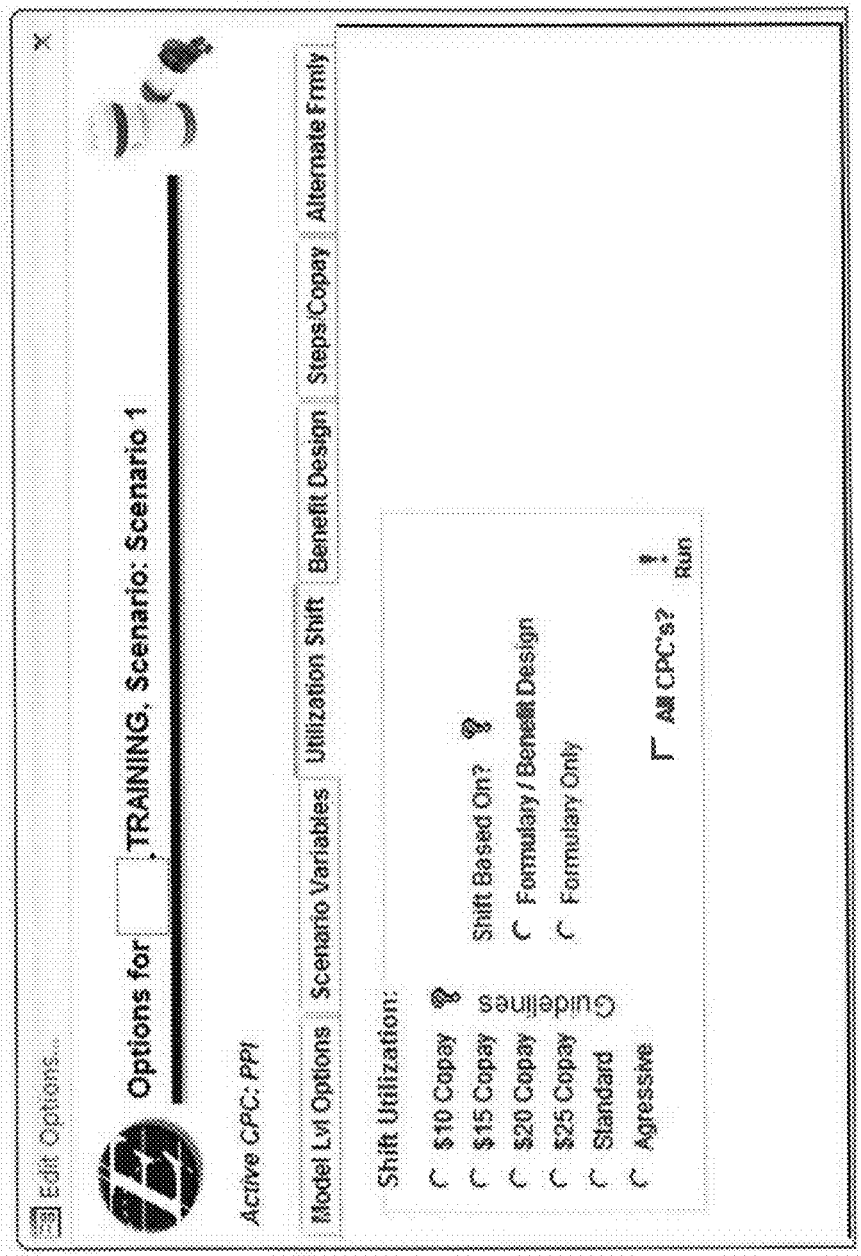

FIG. 28 illustrates a display 2800 produced upon a user's selection of a Utilization Shift tab. In some embodiments, display 2800 facilitates input of utilization shifts in drugs to further enhance and refine the financial modeling features. At display 2800, utilization shift selections may be implemented for a single drug call or for all drug classes. A utilization shift functionality allows a client to assume a general utilization shift based on a given benefit design. The system may incorporate pre-determined utilization shift assumptions and a utilization shift feature may allow a user to override those assumptions.

Figure 29:
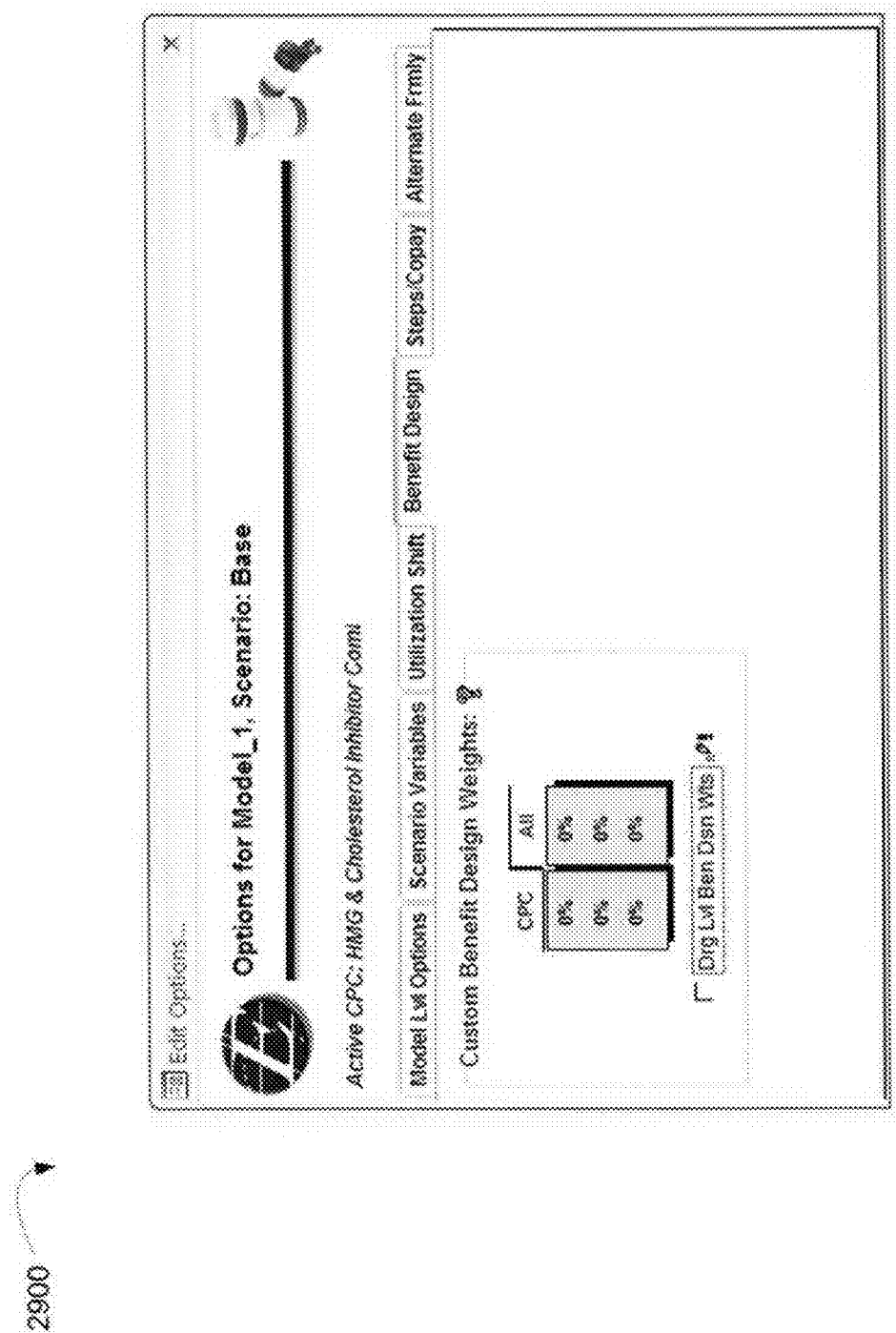

FIG. 29 illustrates a display 2900 producted upon a user's selection of a Benefit Design tab. In this example, benefit design can be changed for one drug class (by using, in this example, the CPD column) or all drug classes. Specifically, a user can enter an amount (e.g., expressed as a percentage) of prescriptions within a particular type of benefit design (e.g., moderate, high, or closed) for a particular drug class or (by using, in this example, the All column) for all drug classes.

Figure 30:
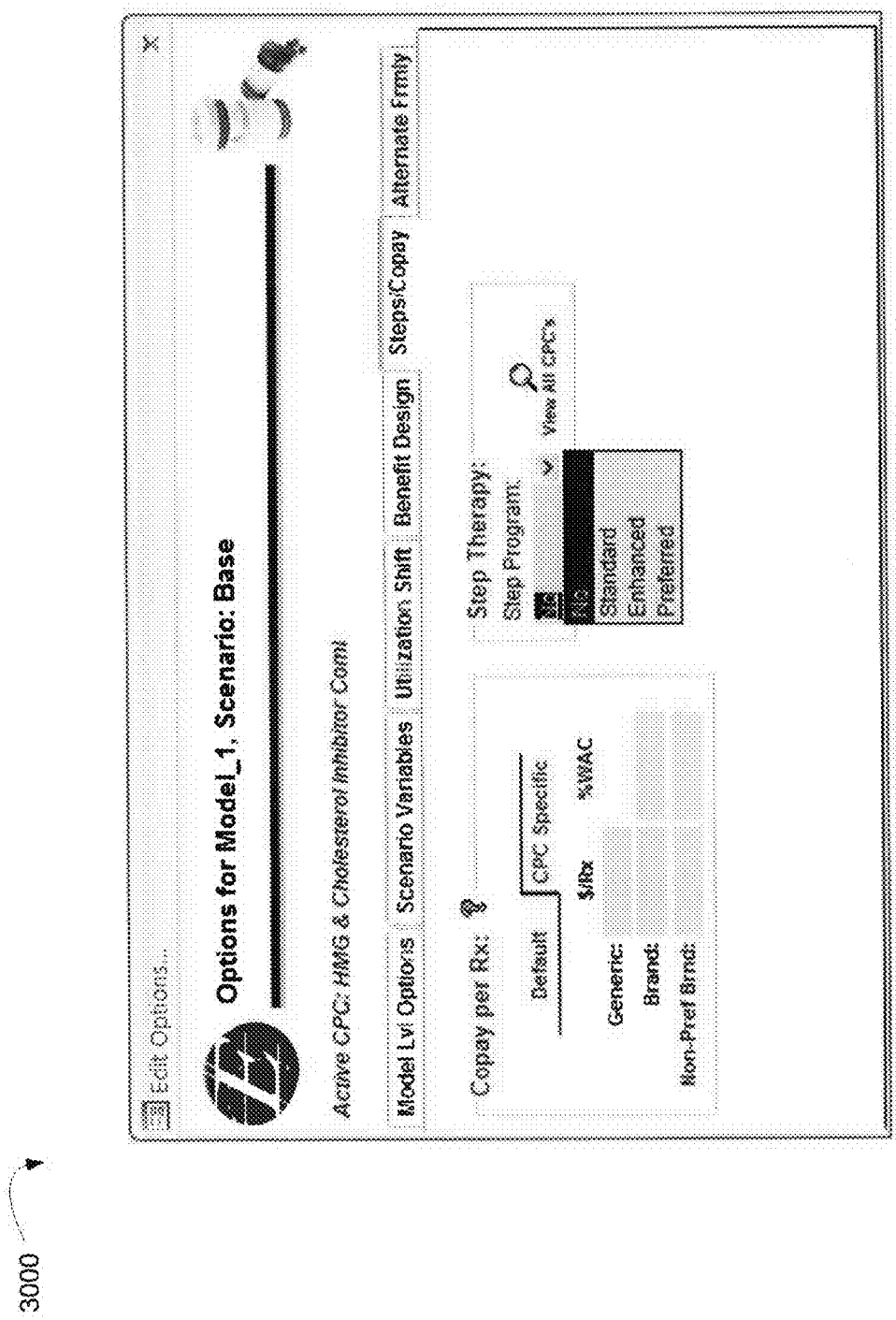

FIG. 30 illustrates a display 3000 producted upon a user's selection of a Steps/Copay tab. In the example illustrated in FIG. 14, the copay can be set for Default or Drug Class Specific. If Default is selected, the selected default will apply to the entire model. If Drug Class Specific is selected, it will apply only for the selected drug class.

Figure 31:
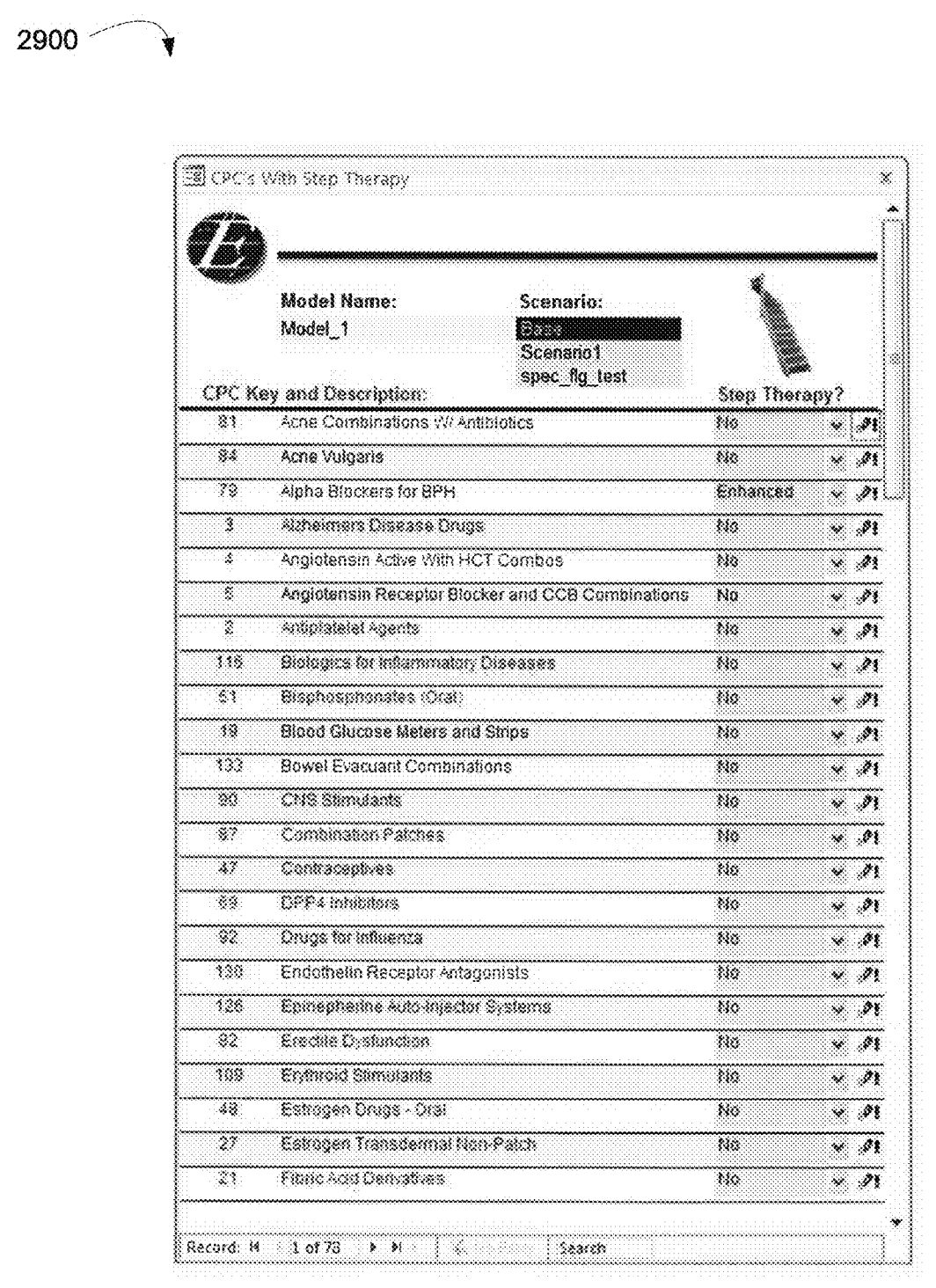

A step therapy portion of display 3000 allows a user to select a particular type of step therapy to be implemented in a pharmaceutical benefit plan design. Selections may be made based on a single drug class or all drug classes. In this embodiment, selection of all drug classes prompts display 3100 of all step therapy options for all drug classes, as illustrated in FIG. 31.

A co-pay per prescription function of display 3000 allows a user to input the actual co-pays into a model in order to determine financial impact to the member and the client. An example co-pay model may be a $5.00 co-pay for a generic drug, a $10.00 co-pay for a brand drug that is on formulary, and a $20.00 co-pay for a brand drug that is not on formulary. Other co-pay models may be used. For example, a co-pay may be based on a percentage of WAC otherwise known as coinsurance. Co-pays may be applied to a particular drug class or to all drug classes.

Figure 32:
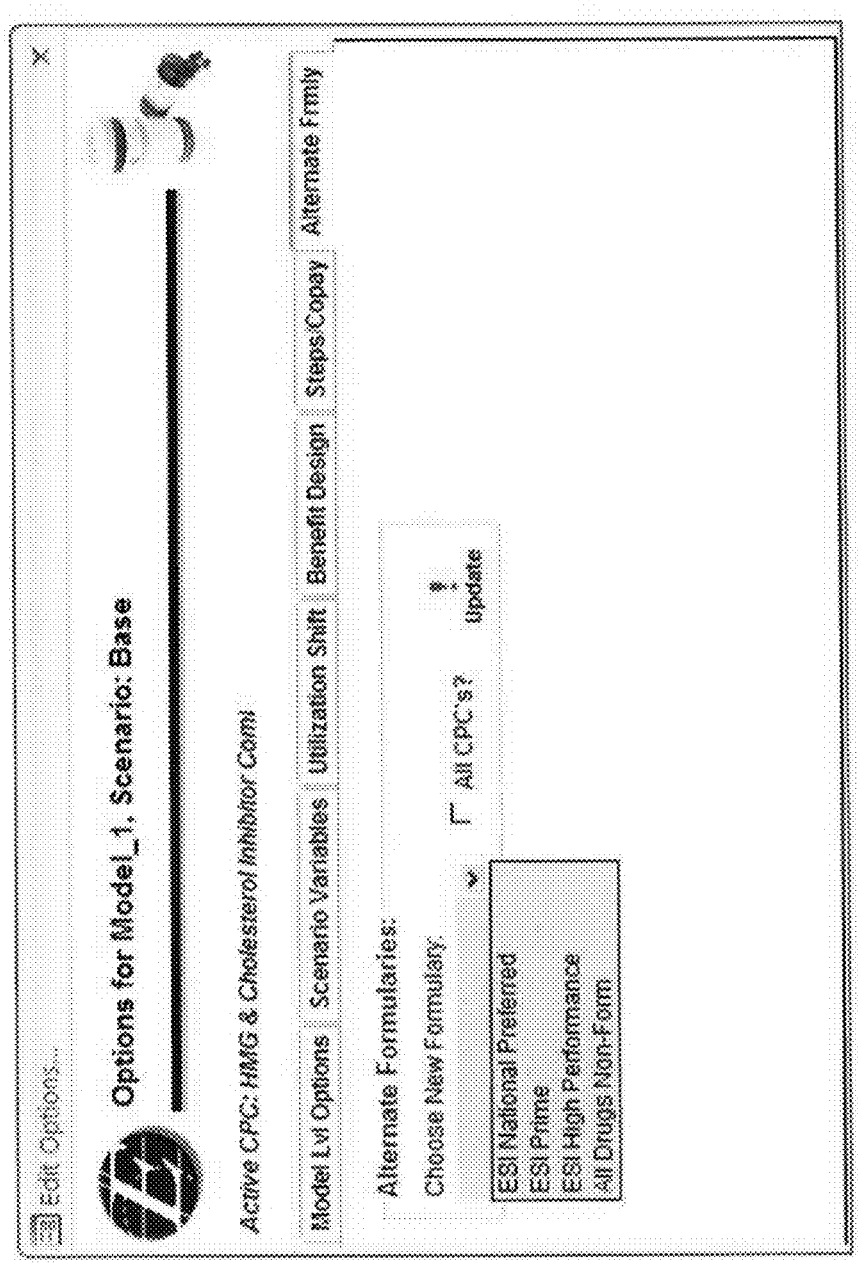

FIG. 32 illustrates a display 3200 producted upon a user's selection of a Alternate Frmly tab (Frmly represents Formulary). Display 3200 includes a portion that allows a user to choose a formulary within the model. For example, a user may be able to access this tool to compare financial impact of plan designs depending upon a particular formulary selected via a drop down menu displayed under the heading Choose New Formulary. In one example, a subsequent year's formulary may be included as an option to allow a user to identify likely formularly changes.

In an example embodiment, a client that has different divisions with different types of benefits may be modeled individually but associated with one another so that, for example, a formulary change to one model may be applied to models for all client divisions (or selected client divisions).

Figure 33:
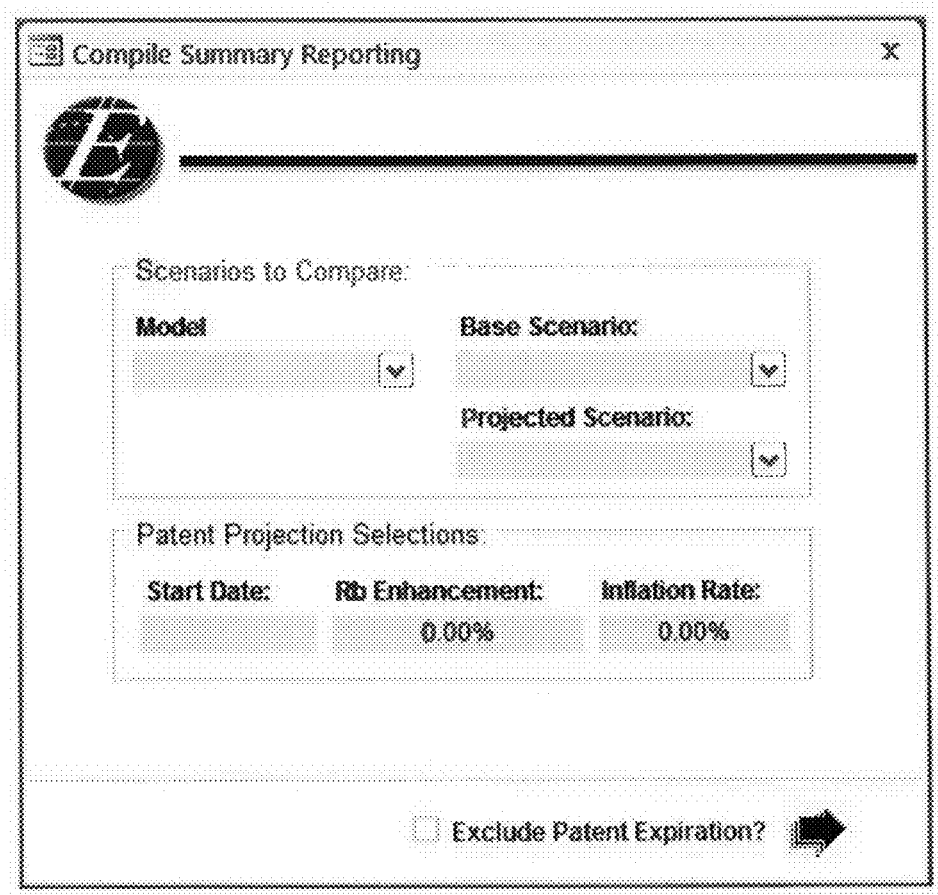

In an example embodiment, a display 3300, as illustrated in FIG. 33, allows a user to view and/or generate a report based on a comparison of selected scenarios to determine the overall financial impact of the changes made from one scenario to another. In this example, a user may enter in a start date (e.g., the start date may be the effective date of the guarantee being projected); the anticipated year over year rebate enhancement (e.g., by populating a rebate enhancement section); and an inflation rate (e.g., the average percent anticipated for inflation for all drugs).

Figure 34:
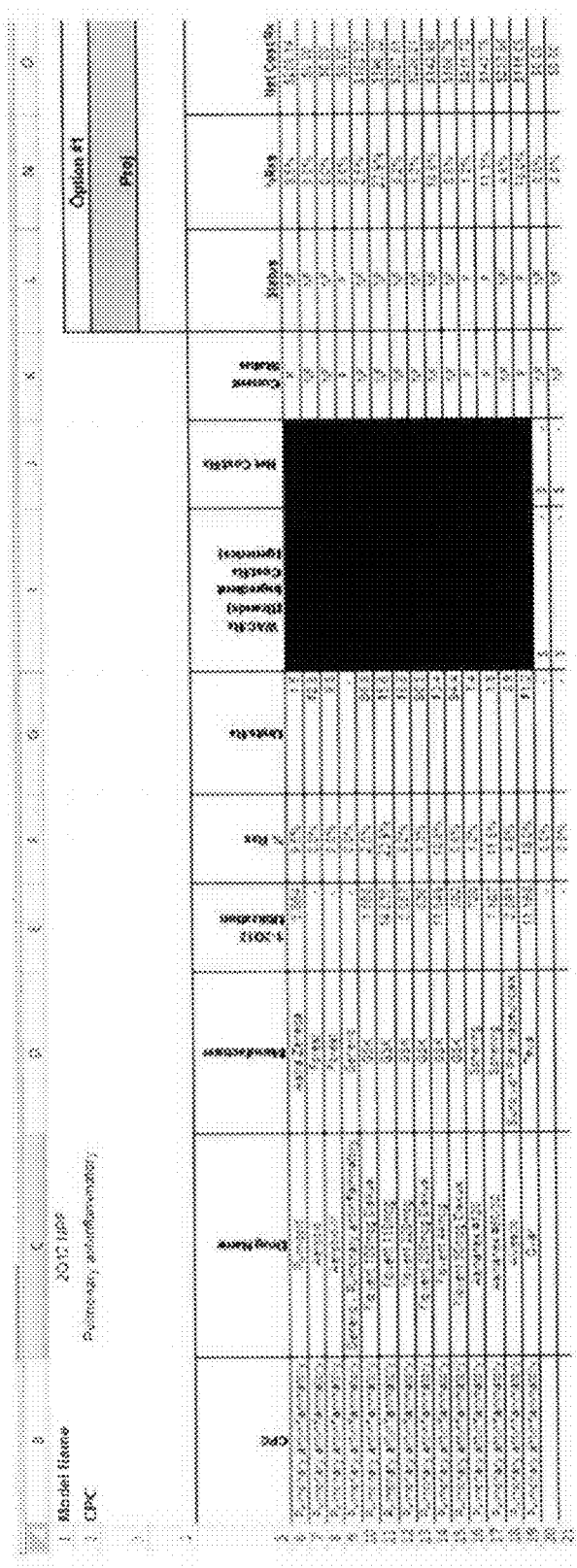
Figure 35:
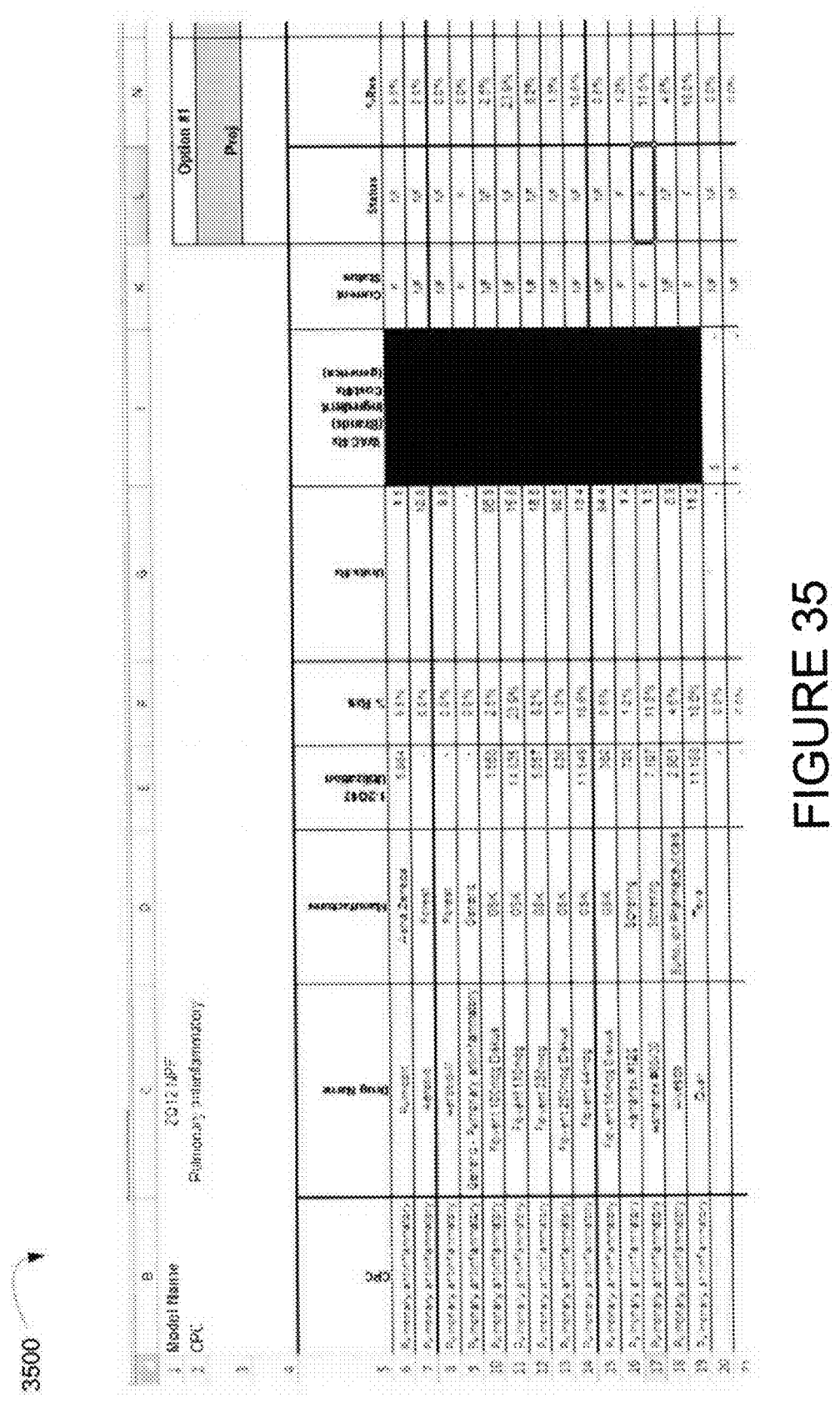
Figure 36:
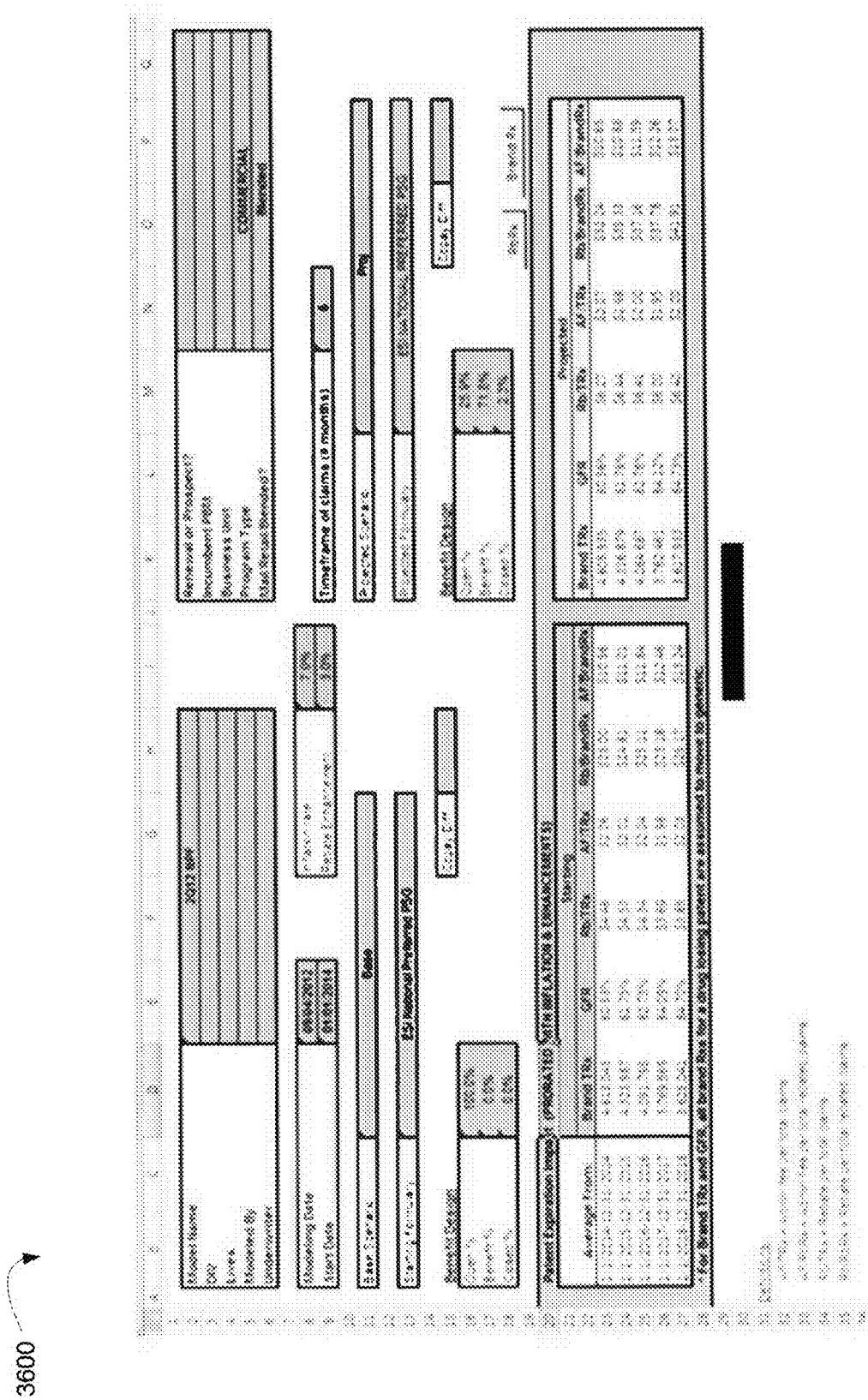

FIGS. 34-36 are examples of reports that may be generated by the rebated modeling subsystem 202. Report 3400 of FIG. 34 is an example of a benefit manager report, report 3500 of FIG. 35 is an example of a client summary report, and report 3600 of FIG. 36 is an example of a 5 year rebate projection report.

Figure 37:
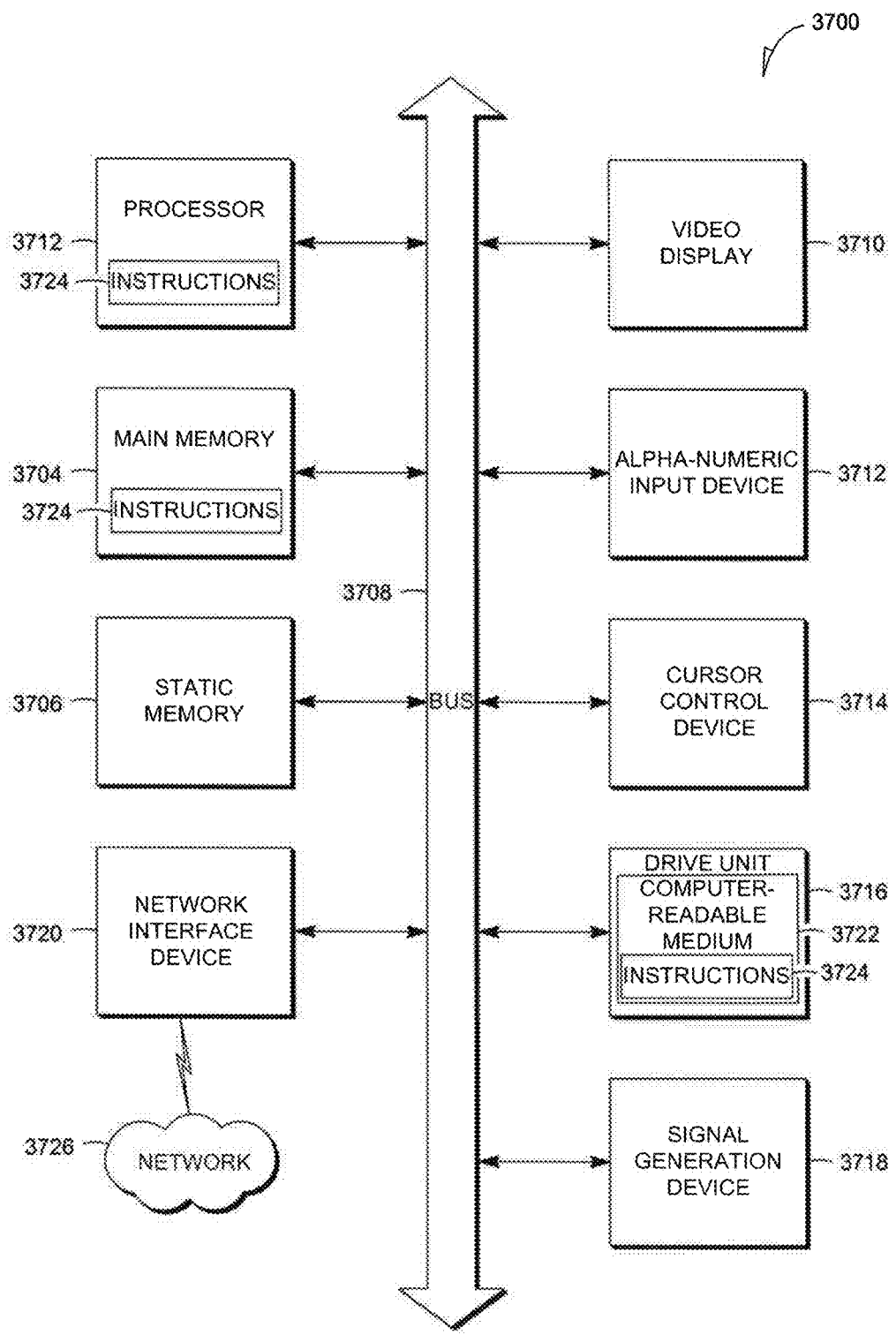
FIG. 37 is a block diagram of a machine in the example form of a computer system within which a set of instructions for causing the machine to perform any one or more of the methodologies discussed herein may be executed or stored.

FIG. 37 shows a block diagram of a machine in the example form of a computer system 3700 within which a set of instructions may be executed causing the machine to perform any one or more of the methods, processes, operations, or methodologies discussed herein. The operator device 102, the benefit management device 106, and the plan design device 108 may include the functionality of the one or more computer systems 3700.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 3700 includes a processor 3712 (e.g., a central processing unit (CPU) a graphics processing unit (GPU) or both), a main memory 3704 and a static memory 3706, which communicate with each other via a bus 3708. The computer system 3700 may further include a video display unit 3710 (e.g., a liquid crystal display (LCD) or a cathode ray tube (CRT)). The computer system 3700 also includes an alphanumeric input device 3712 (e.g., a keyboard), a cursor control device 3714 (e.g., a mouse), a drive unit 3716, a signal generation device 3718 (e.g., a speaker) and a network interface device 3720.

The drive unit 3716 includes a computer-readable medium 3722 on which is stored one or more sets of instructions (e.g., software 3724) embodying any one or more of the methodologies or functions described herein. The software 3724 may also reside, completely or at least partially, within the main memory 3704 and/or within the processor 3712 during execution thereof by the computer system 3700, the main memory 3704 and the processor 3712 also constituting computer-readable media. In some embodiments, the computer-readable medium 3722 is a non-transitory computer-readable medium.

The software 3724 may further be transmitted or received over a network 3726 via the network interface device 3720.

While the computer-readable medium 3722 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media.

In an example embodiment, a formulary of a plan sponsor is accessed. The prescription drug utilization data is accessed. The prescription drug utilization data includes historic prescription drug information for a plurality of patients of the plan sponsor. The historic prescription drug information of a prescription drug of a patient that identifies a drug name of the prescription drug, and a prescription drug unit of the prescription drug, a number of days supply of the prescription drug, and a fill location type. Drug pricing information is accessed. Benefit design including co-pay structure of the plan sponsor is accessed. A plan sponsor rebate for a drug classification is calculated based on the formulary, the prescription drug utilization associated with the drug classification, the drug pricing information associated with a plurality of drugs including the drug classification, and the co-pay structure. An alternate plan sponsor rebate is calculated based on a formulary modification, a benefit design modification, or both the formulary modification and the benefit design modification. A difference between the plan sponsor rebate and alternate plan sponsor rebate is determined. A display based on a determination of the difference is generated.

In an example embodiment, a formulary of a plan sponsor is accessed. Prescription drug utilization data is accessed. The prescription drug utilization data includes historic prescription drug information for a plurality of patients of the plan sponsor. The historic prescription drug information of a prescription drug of a patient identifies a drug name of the prescription drug, and a prescription drug unit of the prescription drug, a number of days supply of the prescription drug, and a fill location type. Drug pricing information is accessed. Benefit design including co-pay structure of the plan sponsor is accessed. Projected drug inflation information, rebate enhancements, and patent expiration information is accessed. Future rebate information of the plan sponsor is projected based on the formulary, the prescription drug utilization associated with the drug classification, the drug pricing information associated with a plurality of drugs including the drug classification, the co-pay structure, the projected drug inflation information, the rebate enhancements, and the patent expiration information.

The term "based on" or using, as used herein, reflects an open-ended term that can reflect others elements beyond those explicitly recited.

Thus, methods and systems for rebate modeling have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion.

What is claimed is:
1. A method comprising:
   receiving, by a processor of a plan design device, a formulary of a plan sponsor from a benefit manager server over the Internet;
   receiving, by the processor of the plan design device, prescription drug utilization data, the prescription drug utilization data including historic prescription drug information of a plurality of patients of the plan sponsor, the historic prescription drug information of a prescription drug of a patient identifying a drug name of the prescription drug, a prescription drug unit of the prescription drug, a number of days' supply of the prescription drug, and a fill location type from a database over the Internet;
   receiving, by the processor of the plan design device, drug pricing information;
   receiving, by the processor of the plan design device, a benefit design of the plan sponsor from a benefit manager server over the Internet, the benefit design including a co-pay structure, wherein the co-pay structure is defined based on a moderate benefit design weight, a high benefit design weight, a closed benefit design weight, a moderate benefit rebate rate, a high benefit rebate rate, and a closed benefit rebate rate, and wherein the co-pay structure is calculated by finding a first product by multiplying the moderate benefit design weight and the moderate benefit rebate rate, finding a second product by multiplying the high benefit design weight and the high benefit rebate rate, and a third product by multiplying the closed benefit design weight and the closed high rebate rate and finding a sum of the first product, the second product, and the third product;

determining by a modification module, a drug classification according to the prescription drug information or a user input;

modeling, by the processor of the plan design device, a plan sponsor rebate for the drug classification based on a first set of data that includes the formulary of the plan sponsor, the prescription drug utilization associated with the drug classification, the drug pricing information associated with a plurality of drugs included within the drug classification, and the co-pay structure included in the benefit design of the plan sponsor;

dynamically modeling, by the processor of the plan design device, an alternate plan sponsor rebate for the drug classification based on an automatically modified set of data, different from the first set of data, that includes the formulary of the plan sponsor, the prescription drug utilization associated with the drug classification, the drug pricing information associated with the plurality of drugs included within the drug classification, and the co-pay structure included in the benefit design of the plan sponsor and a drug-level formulary modification to the formulary of the plan sponsor, a drug-level benefit design modification to the benefit design of the plan sponsor, or both the formulary modification and the benefit design modification wherein the benefit design modification includes a step therapy applied to the drug classification, wherein dynamically modeling the alternate plan sponsor rebate includes automatically applying enhancements, applying enhanced rates, altering the formulary of the plan sponsor, and adjusting a plurality of rebates associated with the drug classification, and wherein dynamically modeling the alternate plan sponsor rebate further includes providing real-time inputs on a graphical user interface to change at least one component of the modified set of data to produce a real-time change in the dynamically modelled alternate plan sponsor rebate;

determining, by the processor of the plan design device, a difference between the plan sponsor rebate and the alternate plan sponsor rebate;

generating, by the processor of the plan design device, a display based on a determination of the difference, the display including the plan sponsor rebate and the alternate plan sponsor rebate;

transmitting instructions from the plan design device to an operator device to output the display on an output screen of the operator device; and transmitting, by the processor of the plan design device, the plan sponsor rebate and the alternate plan sponsor rebate to an underwriting device, the underwriting device configured to determine an effect on a client guarantee based on the plan sponsor rebate and the alternate plan sponsor rebate.

2. The method of claim 1, wherein the formulary modification includes adding an additional prescription drug within the drug classification to the formulary of the plan sponsor.

3. The method of claim 1, wherein the formulary modification includes removing an existing prescription drug within the drug classification from the formulary of the plan sponsor.

4. The method of claim 1, wherein the benefit design modification includes a market share modification applied to the drug classification, wherein dynamically modelling the alternate plan sponsor rebate includes automatically applying exclusions based on a plan sponsor contract.

5. The method of claim 1, further comprising:
receiving a selection of a drug therapy class; and
receiving a selection of a fill location type,
wherein accessing the prescription utilization data is based on the receipt of the selection of the drug therapy class and the fill location type, the prescription utilization data being accessed including only a portion of available prescription utilization data that matches the drug therapy class and the fill location type.

6. The method of claim 5, further comprising:
receiving a selection of a plan sponsor specific model option;
receiving a selection of a scenario model option;
receiving a selection of a co-pay option associated with the drug therapy class; and
receiving a selection of a rate parameter option.

7. The method of claim 6, wherein the drug therapy class is defined according to a condition that the prescription drug is used to treat.

8. The method of claim 1, further comprising:
accessing sponsor rebate data associated with the plan sponsor, the sponsor rebate data including an indicia of a rebate enhancement provided by a manufacturer of the prescription drug to the plan sponsor,
wherein modeling of the plan sponsor rebate is further based on the formulary position of the prescription drug and the rebate enhancement, and
wherein dynamically modelling of the alternate plan sponsor rebate is further based on the modification to the formulary position of the drug and the rebate enhancement.

9. The method of claim 1, further comprising:
accessing benefit manager rebate data associated with a benefit manager, the benefit manager data including an indicia of a rebate enhancement provided by a manufacturer of the prescription drug to the benefit manager of a drug benefit offered through the plan sponsor,
wherein projection of the plan sponsor rebate is further based on the formulary position of the prescription drug and the rebate enhancement, and
wherein projection of the alternate plan sponsor rebate is further based on the modification to the formulary position of the drug and the rebate enhancement.

10. The method of claim 1, wherein the prescription drug utilization information is associated with a particular client, a particular grouping of clients, or a particular book of business.

11. The method of claim 1, wherein accessing the prescription drug utilization data comprises:
processing patient drug utilization data to identify the prescription drug utilization data; and
accessing the prescription drug utilization data among the patient drug utilization data based on identification of the prescription drug utilization data.

12. The method of claim 1, wherein the prescription drug utilization data is at the National Drug Code 11 (NDC11) and mail/retail level.

13. The method of claim 1, wherein the historic prescription drug information of the prescription drug of the patient identifies a benefit tier at which the prescription drug was filled.

14. The method of claim 1, wherein the fill location type is a retail pharmacy fill or a mail order pharmacy fill.

15. The method of claim 1, wherein the formulary of the plan sponsor is a custom formulary of the plan sponsor.

16. The method of claim 1, wherein the plan sponsor rebate and the alternate plan sponsor rebate are for a same, single drug classification.

17. The method of claim 1, wherein the plan sponsor rebate is associated with a base scenario of a model and the alternate plan sponsor rebate is associated with a different scenario of the model.

18. The method of claim 1, further comprising:
receiving an average wholesale price discount at retail selection and an average wholesale price discount at mail selection,
wherein modeling of the plan sponsor rebate and the alternate plan sponsor rebate for the drug classification is further based on the average wholesale price discount at retail selection and the average wholesale price discount at mail selection.

19. The method of claim 1, further comprising:
receiving a simulated formulary change to the formulary,
wherein the formulary modification to the formulary of the plan sponsor is the simulated formulary change to the formulary.

20. The method of claim 1 further comprising:
receiving utilization shift information to reflect a shift of market share of a plurality of prescription drugs included within the prescription drug information,
wherein dynamically modelling of the alternate plan sponsor rebate is further based on receipt of the utilization shift information.

21. The method of claim 1, wherein the display includes identification of a plurality of drugs included within the drug classification, identification of each of the plurality of drugs as being a specialty drug or a non-specialty drug, a total script count for each of the plurality of drugs, and a rebate variance for each of the plurality of drugs.

22. The method of claim 1, wherein projecting the plan sponsor rebate includes determining whether a formulary position on the formulary for each of a plurality of prescription drugs included in the prescription drug utilization data for the drug classification is classified as limited, preferred, or exclusive, and
wherein dynamically modelling the alternate plan sponsor rebate includes determining whether a formulary position on the formulary as modified by the formulary modification for each of the plurality of prescription drugs included in the prescription drug utilization data for the drug classification is classified as limited, preferred, or exclusive.

* * * * *